US008318430B2

(12) United States Patent
Chuu et al.

(10) Patent No.: US 8,318,430 B2
(45) Date of Patent: Nov. 27, 2012

(54) METHODS OF FETAL ABNORMALITY DETECTION

(75) Inventors: Yue-Jen Chuu, Cupertino, CA (US); Richard P. Rava, Redwood City, CA (US)

(73) Assignee: Verinata Health, Inc., Redwood City, CA (US)

( * ) Notice: Subject to any disclaimer, the term of this patent is extended or adjusted under 35 U.S.C. 154(b) by 0 days.

(21) Appl. No.: 13/368,035

(22) Filed: Feb. 7, 2012

(65) Prior Publication Data

US 2012/0135872 A1    May 31, 2012

Related U.S. Application Data

(63) Continuation of application No. 13/012,222, filed on Jan. 24, 2011.

(60) Provisional application No. 61/297,755, filed on Jan. 23, 2010.

(51) Int. Cl.
*C12Q 1/68* (2006.01)
*C12P 19/34* (2006.01)

(52) U.S. Cl. .................... 435/6.1; 435/91.2
(58) Field of Classification Search .............. None
See application file for complete search history.

(56) References Cited

U.S. PATENT DOCUMENTS

| | | | |
|---|---|---|---|
| 5,994,057 A | 11/1999 | Mansfield | |
| 6,258,540 B1 | 7/2001 | Lo et al. | |
| 6,632,655 B1 | 10/2003 | Mehta et al. | |
| 6,927,028 B2 | 8/2005 | Dennis et al. | |
| 7,252,946 B2 | 8/2007 | Szasz | |
| 7,332,277 B2 | 2/2008 | Dhallan | |
| 7,442,506 B2 | 10/2008 | Dhallan | |
| 7,582,420 B2 | 9/2009 | Oliphant et al. | |
| 7,645,576 B2 | 1/2010 | Lo et al. | |
| 7,727,720 B2 | 6/2010 | Dhallan et al. | |
| 7,799,531 B2 | 9/2010 | Mitchell et al. | |
| 7,838,647 B2 | 11/2010 | Hahn et al. | |
| 7,888,017 B2 | 2/2011 | Quake et al. | |
| 7,955,794 B2 | 6/2011 | Shen et al. | |
| 8,003,354 B2 | 8/2011 | Shen et al. | |
| 8,008,018 B2 | 8/2011 | Quake et al. | |
| 8,137,912 B2 | 3/2012 | Stoughton et al. | |
| 8,168,389 B2 | 5/2012 | Shoemaker et al. | |
| 8,195,415 B2 | 6/2012 | Fan et al. | |
| 2001/0051341 A1 | 12/2001 | Lo et al. | |
| 2002/0142324 A1 | 10/2002 | Wang et al. | |
| 2002/0164816 A1 | 11/2002 | Quake | |
| 2003/0022207 A1 | 1/2003 | Balasubramanian | |
| 2003/0044388 A1 | 3/2003 | Dennis et al. | |
| 2003/0194704 A1 | 10/2003 | Penn et al. | |
| 2004/0137470 A1 | 7/2004 | Dhallan | |
| 2004/0209299 A1 | 10/2004 | Pinter et al. | |
| 2005/0196785 A1 | 9/2005 | Quake et al. | |
| 2005/0221341 A1 | 10/2005 | Shimkets et al. | |
| 2005/0252773 A1 | 11/2005 | McBride et al. | |
| 2006/0046258 A1 | 3/2006 | Lapidus et al. | |
| 2006/0257895 A1 | 11/2006 | Pinkel et al. | |
| 2006/0286558 A1 | 12/2006 | Novoradovskaya et al. | |
| 2007/0134658 A1 | 6/2007 | Bohmer et al. | |
| 2007/0202525 A1 | 8/2007 | Quake et al. | |
| 2007/0207466 A1 | 9/2007 | Cantor et al. | |
| 2007/0275402 A1 | 11/2007 | Lo et al. | |
| 2008/0020390 A1 | 1/2008 | Mitchell et al. | |
| 2008/0050739 A1 | 2/2008 | Stoughton et al. | |
| 2008/0064098 A1 | 3/2008 | Allickson | |
| 2008/0070792 A1* | 3/2008 | Stoughton et al. ............ 506/9 |
| 2008/0071076 A1 | 3/2008 | Hahn et al. | |
| 2008/0096216 A1 | 4/2008 | Quake | |
| 2008/0138809 A1 | 6/2008 | Kapur et al. | |
| 2008/0193927 A1 | 8/2008 | Mann et al. | |
| 2008/0220422 A1 | 9/2008 | Shoemaker et al. | |
| 2008/0299562 A1 | 12/2008 | Oeth et al. | |
| 2009/0029377 A1 | 1/2009 | Lo et al. | |
| 2009/0053719 A1 | 2/2009 | Lo et al. | |
| 2009/0087847 A1 | 4/2009 | Lo et al. | |
| 2009/0170114 A1 | 7/2009 | Quake et al. | |
| 2009/0215042 A1 | 8/2009 | Sella-Tavor et al. | |
| 2009/0270601 A1 | 10/2009 | Benner et al. | |
| 2009/0299645 A1 | 12/2009 | Colby et al. | |
| 2009/0307181 A1 | 12/2009 | Colby et al. | |
| 2009/0317798 A1 | 12/2009 | Heid et al. | |
| 2009/0317817 A1 | 12/2009 | Oeth et al. | |
| 2009/0317818 A1 | 12/2009 | Ehrich et al. | |
| 2010/0068711 A1 | 3/2010 | Umansky et al. | |
| 2010/0093550 A1 | 4/2010 | Stuelpnagel et al. | |
| 2010/0093835 A1 | 4/2010 | McSwiggen et al. | |
| 2010/0112575 A1 | 5/2010 | Fan et al. | |
| 2010/0112590 A1 | 5/2010 | Lo et al. | |
| 2010/0136529 A1 | 6/2010 | Shoemaker et al. | |
| 2010/0138165 A1 | 6/2010 | Fan et al. | |
| 2010/0167954 A1 | 7/2010 | Earnshaw et al. | |
| 2010/0184075 A1 | 7/2010 | Cantor et al. | |
| 2010/0216151 A1 | 8/2010 | Lapidus et al. | |
| 2010/0216153 A1 | 8/2010 | Lapidus et al. | |
| 2010/0304978 A1 | 12/2010 | Deng et al. | |
| 2010/0311064 A1 | 12/2010 | Oliphant et al. | |
| 2011/0027771 A1 | 2/2011 | Deng et al. | |

(Continued)

FOREIGN PATENT DOCUMENTS

EP    0994963 B1    5/2003

(Continued)

OTHER PUBLICATIONS

Illuminia. Multiplexed Sequencing with the Illumina Genome Analyzer System. Dec. 2, 2008. Illumina Sequecing. 4 pages.*

(Continued)

*Primary Examiner* — Jennifer Dunston
*Assistant Examiner* — Channing S Mahatan
(74) *Attorney, Agent, or Firm* — Wilson Sonsini Goodrich & Rosati

(57) ABSTRACT

Methods and kits for selectively enriching non-random polynucleotide sequences are provided. Methods and kits for generating libraries of sequences are provided. Methods of using selectively enriched non-random polynucleotide sequences for detection of fetal aneuploidy are provided.

30 Claims, 28 Drawing Sheets

U.S. PATENT DOCUMENTS

| | | | |
|---|---|---|---|
| 2011/0105353 | A1 | 5/2011 | Lo et al. |
| 2011/0117548 | A1 | 5/2011 | Mitchell et al. |
| 2011/0177517 | A1 | 7/2011 | Rava et al. |
| 2011/0201507 | A1 | 8/2011 | Rava et al. |
| 2011/0224087 | A1 | 9/2011 | Quake et al. |
| 2011/0230358 | A1 | 9/2011 | Rava |
| 2011/0245085 | A1 | 10/2011 | Rava et al. |
| 2011/0312503 | A1 | 12/2011 | Chuu et al. |
| 2012/0010085 | A1 | 1/2012 | Rava et al. |
| 2012/0034603 | A1 | 2/2012 | Oliphant et al. |
| 2012/0034685 | A1 | 2/2012 | Sparks et al. |

FOREIGN PATENT DOCUMENTS

| | | | |
|---|---|---|---|
| WO | WO 98/44151 | A1 | 10/1998 |
| WO | WO 00/18957 | A1 | 4/2000 |
| WO | WO 03/020974 | A2 | 3/2003 |
| WO | WO 03/020974 | A3 | 9/2003 |
| WO | WO 2004/065629 | A1 | 8/2004 |
| WO | WO 2005/118852 | A2 | 12/2005 |
| WO | WO 2006/010610 | A2 | 2/2006 |
| WO | WO 2005/118852 | A3 | 3/2006 |
| WO | WO 2006/010610 | A3 | 6/2006 |
| WO | WO 2006/097049 | A1 | 9/2006 |
| WO | WO 2007/044091 | A2 | 4/2007 |
| WO | WO 2007/075836 | A2 | 7/2007 |
| WO | WO 2007/092473 | A2 | 8/2007 |
| WO | WO 2007/100911 | A2 | 9/2007 |
| WO | WO 2007/044091 | A3 | 11/2007 |
| WO | WO 2007/100911 | A3 | 11/2007 |
| WO | WO 2007/132166 | A2 | 11/2007 |
| WO | WO 2007/132167 | A2 | 11/2007 |
| WO | WO 2007/147073 | A2 | 12/2007 |
| WO | WO 2007/147074 | A2 | 12/2007 |
| WO | WO 2007/147076 | A2 | 12/2007 |
| WO | WO 2007/147079 | A2 | 12/2007 |
| WO | WO 2007/075836 | A3 | 2/2008 |
| WO | WO 2007/132166 | A3 | 2/2008 |
| WO | WO 2007/147079 | A3 | 3/2008 |
| WO | WO 2007/147076 | A3 | 4/2008 |
| WO | WO 2008/045158 | A1 | 4/2008 |
| WO | WO 2007/132167 | A3 | 5/2008 |
| WO | WO 2007/147073 | A3 | 5/2008 |
| WO | WO 2007/147074 | A3 | 5/2008 |
| WO | WO 2007/092473 | A3 | 11/2008 |
| WO | WO 2009/013492 | A1 | 1/2009 |
| WO | WO 2009/013496 | A1 | 1/2009 |
| WO | WO 2009/019455 | A2 | 2/2009 |
| WO | WO 2009/019455 | A3 | 4/2009 |
| WO | WO 2010/033578 | A2 | 3/2010 |
| WO | WO 2010/045617 | A2 | 4/2010 |
| WO | WO 2010/033578 | A3 | 5/2010 |
| WO | WO 2010/085815 | A1 | 7/2010 |
| WO | WO 2011/014741 | A1 | 2/2011 |
| WO | WO 2011/051283 | A1 | 5/2011 |
| WO | WO 2011/090556 | A1 | 7/2011 |
| WO | WO 2011/090557 | A1 | 7/2011 |
| WO | WO 2011/090558 | A1 | 7/2011 |
| WO | WO 2011/090559 | A1 | 7/2011 |
| WO | WO 2011/091046 | A1 | 7/2011 |
| WO | WO 2011/091063 | A1 | 7/2011 |
| WO | WO 2011/094646 | A1 | 8/2011 |
| WO | WO 2011/102998 | A2 | 8/2011 |
| WO | WO 2012/019187 | A2 | 2/2012 |
| WO | WO 2012/019193 | A2 | 2/2012 |
| WO | WO 2012/019198 | A2 | 2/2012 |
| WO | WO 2012/019200 | A2 | 2/2012 |

OTHER PUBLICATIONS

Fan et al. Noninvasive diagnosis of fetal aneuploidy by shotgun sequencing DNA from maternal blood. Oct. 21, 2008. Proceedings of the National Academy of Sciences. pp. 16266-16271.*
U.S. Appl. No. 13/191,366, filed Jul. 26, 2011, Rava et al.
U.S. Appl. No. 13/364,809, filed Feb. 2, 2012, Rava et al.
U.S. Appl. No. 13/365,134, filed Feb. 2, 2012, Rava et al.
Bennett, et al. Toward the 1,000 dollars human genome. Pharmacogenomics. 2005; 6(4):373-82.
Fan, et al. Highly parallel genomic assays. Nat Rev Genet. Aug. 2006;7(8):632-44.
Margulies, et al. Genome sequencing in microfabricated high-density picolitre reactors. Nature. 2005; 437:376-80.
Shendure, et al. Next-generation DNA sequencing: Nature. 2008; 26(10):1135-1145.
Yang, et al. Rapid Prenatal Diagnosis of Trisomy 21 by Real-time Quantitative Polymerase Chain Reaction with Amplification of Small Tandem Repeats and S100B in Chromosome 21.Yonsei Medical Journal, 2005, vol. 46, No. 2, 193-197.
Bentley, et al. Accurate whole human genome sequencing using reversible terminator chemistry. Nature. Nov. 6, 2008;456(7218):53-9.
Botezatu, et al. Genetic analysis of DNA excreted in urine: a new approach for detecting specific genomic DNA sequences from cells dying in an organism. Clin Chem. Aug. 2000;46(8 Pt 1):1078-84.
Butler, et al. The development of reduced size STR amplicons as tools for analysis of degraded DNA. J Forensic Sci. Sep. 2003;48(5):1054-64.
Butler. Short tandem repeat typing technologies used in human identity testing. Biotechniques. Oct. 2007;43(4):ii-v.
Chan, et al. Size distributions of maternal and fetal DNA in maternal plasma. Clin Chem. Jan. 2004;50(1):88-92.
Chen, et al. Microsatellite alterations in plasma DNA of small cell lung cancer patients. Nat Med. Sep. 1996;2(9):1033-5.
Chiu, et al. Maternal plasma DNA analysis with massively parallel sequencing by ligation for noninvasive prenatal diagnosis of trisomy 21. Clin Chem. Mar. 2010;56(3):459-63.
Chiu, et al. Non-invasive prenatal assessment of trisomy 21 by multiplexed maternal plasma DNA sequencing: large scale validity study. BMJ. Jan. 11, 2011;342:c7401.
Chiu, et al. Non-invasive prenatal diagnosis by single molecule counting technologies. Trends Genet. Jul. 2009;25(7):324-31.
Chiu, et al. Noninvasive prenatal diagnosis of fetal chromosomal aneuploidy by massively parallel genomic sequencing of DNA in maternal plasma. Proc Natl Acad Sci U S A. Dec. 23, 2008;105(51):20458-63.
Chu, et al. Statistical model for whole genome sequencing and its application to minimally invasive diagnosis of fetal genetic disease. Bioinformatics. May 15, 2009;25(10):1244-50.
Coble, et al. Characterization of new miniSTR loci to aid analysis of degraded DNA. J Forensic Sci. Jan. 2005;50(1):43-53.
Dhallan, et al. A non-invasive test for prenatal diagnosis based on fetal DNA present in maternal blood: a preliminary study. Lancet. Feb. 10, 2007;369(9560):474-81.
Dixon, et al. Analysis of artificially degraded DNA using STRs and SNPs—results of a collaborative European (EDNAP) exercise. Forensic Sci Int. Dec. 1, 2006;164(1):33-44.
Ehrich, et al. Noninvasive detection of fetal trisomy 21 by sequencing of DNA in maternal blood: a study in a clinical setting. Am J Obstet Gynecol. Mar. 2011;204(3):205.e1-11.
Fan, et al. Analysis of the size distributions of fetal and maternal cell-free DNA by paired-end sequencing. Clin Chem. Aug. 2010;56(8):1279-86.
Fan, et al. Detection of aneuploidy with digital polymerase chain reaction. Anal Chem. Oct. 1, 2007;79(19):7576-9.
Fan, et al. In principle method for noninvasive determination of the fetal genome. Nature Precedings: Nature Precedings 10.1038/npre. 2010.5373.1 . 2010.
Fan, et al. Microfluidic digital PCR enables rapid prenatal diagnosis of fetal aneuploidy. Am J Obstet Gynecol. May 2009;200(5):543.e1-7.
Fan, et al. Noninvasive diagnosis of fetal aneuploidy by shotgun sequencing DNA from maternal blood. Proc Natl Acad Sci U S A. Oct. 21, 2008;105(42):16266-71.
Fan, et al. Sensitivity of noninvasive prenatal detection of fetal aneuploidy from maternal plasma using shotgun sequencing is limited only by counting statistics. PLoS One. May 3, 2010;5(5):e10439.
Fan, et al. Whole Genome Molecular Haplotyping of Single Cells. Nat Biotechnol. Jan. 2011;29(1):51-7.
Ghanta, et al. Non-invasive prenatal detection of trisomy 21 using tandem single nucleotide polymorphisms. PLoS One. Oct. 8, 2010;5(10):e13184.

Grubweiser, et al. A new miniSTR-mulitplex displaying reduced amplicon lengths for the analysis of degraded DNA. Int J Legal Med. Mar. 2006;120(2):115-20.

Hanson, et al. Whole genome amplification strategy for forensic genetic analysis using single or few cell equivalents of genomic DNA. Anal Biochem. Nov. 15, 2005;346(2):246-57.

Harris, et al. Single-molecule DNA sequencing of a viral genome. Science. Apr. 4, 2008;320(5872):106-9.

Harrison, et al. Polymer-stimulated ligation: enhanced ligation of oligo- and polynucleotides by T4 RNA ligase in polymer solutions. Nucleic Acids Res. Nov. 12, 1984;12(21):8235-51.

Hayashi, et al. Regulation of inter- and intramolecular ligation with T4 DNA ligase in the presence of polyethylene glycol. Nucleic Acids Res. Oct. 10, 1986;14(19):761731.

Hill, et al. "Characterization of 26 new miniSTR loci" Poster #44—17th International Symposium on Human Identification, Nashville, TN, Oct. 10-12, 2006.

Huang, et al. Isolation of cell-free DNA from maternal plasma using manual and automated systems. Methods Mol Biol. 2008;444:203-8.

Hung, et al. Detection of circulating fetal nucleic acids: a review of methods and applications. J Clin Pathol. Apr. 2009;62(4):308-13.

Illumina. Preparing samples for CHIP sequencing of DNA. Epub at gref.jhmi.edu/hts/protocols/11257047_ChIP_Sample_Prep.pdf. 2007.

International search report and written opinion dated Feb. 28, 2011 for PCT Application No. US10/58606.

International search report and written opinion dated Mar. 1, 2011 for PCT Application No. US10/58614.

International search report and written opinion dated Apr. 4, 2011 for PCT Application No. US10/58609.

International search report and written opinion dated Apr. 11, 2011 for PCT Application No. US11/21729.

International search report dated May 19, 2011 for PCT/US2010/058612.

International. The International HapMap Project. Nature. 2003; 426:789-96.

Jama, et al. Quantification of Cell-Free Fetal DNA Levels in Maternal Plasma by STR Analysis. ACMG Annual Clinical Genetics Meeting Poster 398; Mar. 24-28, 2010. Available online at http://acmg.omnibooksonline.com/2010/data/papers/398.pdf and http://acmg.omnibooksonline.com/2010/index.html.

Jorgez, et al. Improving enrichment of circulating fetal DNA for genetic testing: size fractionation followed by whole gene amplification. Fetal Diagn Ther. 2009;25(3):314-9.

Ju, et al. Four-color DNA sequencing by synthesis using cleavable fluorescent nucleotide reversible terminators. Proc Natl Acad Sci USA. 2006; 103(52):19635-19640.

Kidd, et al. Developing a SNP panel for forensic identification of individuals. Forensic Sci Int. Dec. 1, 2006;164(1):20-32.

Koide, et al. Fragmentation of cell-free fetal DNA in plasma and urine of pregnant women. Prenat Diagn. Jul. 2005;25(7):604-7.

Kozarewa, et al. Amplification-free Illumina sequencing-library preparation facilitates improved mapping and assembly of GC-biased genomes. Nat Methods. Apr. 2009;6(4):291-5.

Lazinski, et al. Modified protocol for Illumina paired-end library construction. Available online at http://genomics.med.tufts.edu/documents/htseq_protocol_for_illumina_paired.pdf Accessed Jun. 21, 2011.

Leon, et al. Free DNA in the serum of cancer patients and the effect of therapy. Cancer Res. Mar. 1977;37(3):646-50.

Levy, et al. The Diploid Genome Sequence of an Individual Human. PLoS Biol. 2007 Sep 4;5(10):e254.

Li, et al. Size separation of circulatory DNA in maternal plasma permits ready detection of fetal DNA polymorphisms. Clin Chem. Jun. 2004;50(6):1002-11.

Liao, et al. Targeted massively parallel sequencing of maternal plasma DNA permits efficient and unbiased detection of fetal alleles. Clin Chem. Jan. 2011;57(1):92-101.

Liu, et al. Feasibility study of using fetal DNA in maternal plasma for non-invasive prenatal diagnosis. Acta Obstet Gynecol Scand. 2007;86(5):535-41.

Lo, et al. Digital PCR for the molecular detection of fetal chromosomal aneuploidy. Proc Natl Acad Sci U S A. Aug. 7, 2007;104(32):13116-21.

Lo, et al. Increased fetal DNA concentrations in the plasma of pregnant women carrying fetuses with trisomy 21. Clin Chem. Oct. 1999;45(10):1747-51.

Lo, et al. Maternal plasma DNA sequencing reveals the genome-wide genetic and mutational profile of the fetus. Sci Transl Med. Dec. 8, 2010;2(61):61ra91.

Lo, et al. Presence of fetal DNA in maternal plasma .Lancet. Aug. 16, 1997;350(9076):485-7.

Lo, et al. Quantitative analysis of fetal DNA in maternal plasma and serum: implications for noninvasive prenatal diagnosis. Am J Hum Genet. Apr. 1998;62(4):768-75.

Lo, et al. Rapid clearance of fetal DNA from maternal plasma. Am J Hum Genet. Jan. 1999;64(1):218-24.

Lo, Y. M. Noninvasive prenatal detection of fetal chromosomal aneuploidies by maternal plasma nucleic acid analysis: a review of the current state of the art. BJOG, 2009, vol. 116, 152-157.

Lun, et al. Microfluidics Digital PCR Reveals a Higher than Expected Fraction of Fetal DNA in Maternal Plasma. Clinical Chemistry, 2008, vol. 54, No. 10, 1664-1672.

McKernan, et al. Sequence and structural variation in a human genome uncovered by short-read, massively parallel ligation sequencing using two-base encoding. Genome Res. Sep. 2009;19(9):1527-41.

Metzker. Sequencing technologies—the next generation. Nat Rev Genet. Jan. 2010;11(1):31-46.

Nakamoto, et al. Detection of microsatellite alterations in plasma DNA of malignant mucosal melanoma using whole genome amplification. Bull Tokyo Dent Coll. May 2008;49(2):77-87.

Nicklas, et al. A real-time multiplex SNP melting assay to discriminate individuals. J Forensic Sci. Nov. 2008;53(6):1316-24.

Pakstis, et al. Candidate SNPs for a universal individual identification panel. Hum Genet. May 2007;121(3-4):305-17.

Pakstis, et al. SNPs for a universal individual identification panel. Hum Genet. Mar. 2010;127(3):315-24.

Pathak, et al. Circulating cell-free DNA in plasma/serum of lung cancer patients as a potential screening and prognostic tool. Clin Chem. Oct. 2006;52(10):1833-42.

Pertl, et al. Detection of male and female DNA in maternal plasma by multiplex fluorescent polymerase chain reaction amplification of short tandem repeats. Hum Genet. Jan. 2000;106(1):45-9.

Pheiffer, et al. Polymer-stimulated ligation: enhanced blunt- or cohesive-end ligation of DNA or deoxyribooligonucleotides by T4 DNA ligase in polymer solutions. Nucleic Acids Res. Nov. 25, 1983;11(22):7853-71.

Pushkarev, et al. Single-molecule sequencing of an individual human genome. Nat Biotechnol. Sep. 2009;27(9):847-50.

Quail, et al. A large genome center's improvements to the Illumina sequencing system. Nat Methods. Dec. 2008;5(12):1005-10.

Schwartzenbach, et al. Cell-free tumor DNA in blood plasma as a marker for circulating tumor cells in prostate cancer. Clin Cancer Res. Feb. 1, 2009;15(3):1032-8.

Schwartzenbach, et al. Comparative evaluation of cell-free tumor DNA in blood and disseminated tumor cells in bone marrow of patients with primary breast cancer. Breast Cancer Res. 2009;11(5):R71.

Su, et al. Human urine contains small, 150 to 250 nucleotide-sized, soluble DNA derived from the circulation and may be useful in the detection of colorectal cancer. J Mol Diagn. May 2004;6(2):101-7.

Tong, et al. Noninvasive prenatal detection of trisomy 21 by an epigenetic-genetic chromosome-dosage approach. Clin Chem. Jan. 2010;56(1):90-8.

Vallone, et al. Demonstration of rapid multiplex PCR amplification involving 16 genetic loci. Forensic Sci Int Genet. Dec. 2008;3(1):42-5.

Voelkerding, et al. Digital Fetal Aneuploidy Diagnosis by Next-Generation Sequencing. Clin Chem. Mar. 2010;56(3):336-8.

Voelkerding, et al. Next-generation sequencing: from basic research to diagnostics Clin Chem. Apr. 2009;55(4):641-58.

Wheeler, et al. The complete genome of an individual by massively parallel DNA sequencing. Nature. Apr. 17, 2008;452(7189):872-6.

Wright, et al. The use of cell-free fetal nucleic acids in maternal blood for non-invasive prenatal diagnosis. Hum Reprod Update. Jan.-Feb. 2009;15(1):139-51.

Zimmerman, et al. Macromolecular crowding allows blunt-end ligation by DNA ligase from rat liver of *Escheridia coli*. Proc Natl Acad Sci U S A. Oct. 1983;80(19):5852-6.

U.S. Appl. No. 13/333,832, filed Dec. 21, 2011, Rava et al.

U.S. Appl. No. 13/365,240, filed Feb. 2, 2012, Quake et al.

U.S. Appl. No. 13/433,232, filed Mar. 28, 2012, Stoughton et al.

European Patent Office Communication dated Mar. 16, 2012 in EP App. No. 10830938.6 (EP Publication No. 2366031) with pending claims, 9 pages.

European Patent Office Communication dated Mar. 16, 2012 in EP App. No. 10830939.4 (EP Publication No. 2376661) with pending claims, 9 pages.

European Patent Office Communication dated Mar. 19, 2012 in EP App. No. 10825822.9 (EP Publication No. 2370599) with pending claims, 10 pages.

European Supplementary Search Report for EP App. No. 10830938.6 (EP Publication No. 2366031), dated Feb. 22, 2012, 4 pages.

European Supplementary Search Report for EP App. No. 10825822.9 (EP Publication No. 2370599), dated Feb. 22, 2012, 4 pages.

European Supplementary Search Report for EP App. No. 10830939.4 (EP Publication No. 2376661), dated Feb. 22, 2012, 4 pages.

Lo, et al. Non-invasive prenatal diagnosis of fetal chromosomal aneuploidies by maternal plasma nucleic acid analysis. Clinical Chemistry. 2008; 54 (3):461-466.

U.S. Appl. No. 13/452,083, filed Apr. 20, 2012, Fan et al.

Notice of allowance dated Jul. 12, 2012 for U.S. Appl. No. 13/452,083.

Office action dated Jun. 5, 2012 for U.S. Appl. No. 12/393,833.

* cited by examiner

Figure 3

| Primer | 24107 | 11215 | 11205 | ID of Plasma DNA 24101 | 24102 | 24103 | 24111 | 24106 | Genomic DNA Non-Pregnant |
|---|---|---|---|---|---|---|---|---|---|
| 1_150 | 12.48 | 13.87 | 15.27 | 9.49 | 11.47 | 15.13 | 10.94 | 16.44 | 24.31 |
| 3_150 | 15.63 | 9.34 | 10.32 | No Data | 9.11 | 13.43 | 16.39 | 11.58 | 22.97 |
| 4_150 | 14.33 | 7.78 | 8.55 | No Data | 7.18 | 10.17 | 12.18 | 10.12 | 22.52 |
| 6_150 | 9.47 | 9.57 | 7.91 | 6.6 | 9.4 | 10.24 | 10.07 | No Data | 20.57 |
| 5_150 | 4.83 | 3.08 | 3.39 | 3.82 | 4.2 | 3.74 | 9.46 | 8.31 | 12.82 |
| 2_150 | 7.81 | 5.85 | 5.19 | No Data | 4.59 | 6.19 | 11.08 | 9.07 | 8.81 |
| 7_150 | 2.27 | 3.75 | 3.91 | 2.63 | 4.71 | 4.01 | 4.59 | No Data | 8.16 |

ND: Not Detectable
Conc. ng / ul

Figure 5

| Sample ID | Ch21 Primer | Conc. ng/ul |
|---|---|---|
| 1 | 1_150 | 10.94 |
| 1 | 2_150 | 11.08 |
| 1 | 3_150 | 16.39 |
| 1 | 4_150 | 12.18 |
| 1 | 5_150 | 9.46 |
| 2 | 1_150 | 16.44 |
| 2 | 2_150 | 9.07 |
| 2 | 3_150 | 11.58 |
| 2 | 4_150 | 10.12 |
| 2 | 5_150 | 8.31 |
| 3 | 1_150 | 11.72 |
| 3 | 2_150 | 8.66 |
| 3 | 3_150 | 11.32 |
| 3 | 4_150 | 9.93 |
| 3 | 5_150 | 9.69 |

Figure 8

| A | | ch1 dPCR counts | ch521 dPCR counts | Ch21 / Ch1 Ratio |
|---|---|---|---|---|
| Ch21_1 / Ch1 | 24 t21, PCR Enrichment<br>Ch1_1<br>Ch21_1<br>Ch21_1 / Ch1_1<br>24 t21, cf plasma DNA<br>Ch1_1<br>Ch21_1 | 0<br><br>21 × 5 × 10³<br>595 | 463 × 5 × 10³<br>311 × 5 × 10³<br><br>382 | 463 × 5 × 10³<br>14.81<br><br>1.63 |
| Ch21_2 / Ch1 | 24 t21, PCR Enrichment<br>Ch1_1<br>Ch21_2<br>Ch21_2 / Ch1_1<br>24 t21, cf plasma DNA<br>Ch1_1<br>Ch21_2 | 0<br><br>10 × 5 × 10³<br>177 | 108 × 5 × 10³<br>54 × 5 × 10³<br><br>236 | 108 × 5 × 10³<br>5.4<br><br>1.33 |
| Ch21_5 / Ch1 | 24 t21, PCR Enrichment<br>Ch1_1<br>Ch21_5<br>Ch21_5 / Ch1_1<br>24 t21, cf plasma DNA<br>Ch1_1<br>Ch21_5 | 0<br><br>10 × 5 × 10³<br>212 | 44 × 5 × 10³<br>98 × 5 × 10³<br><br>332 | 44 × 5 × 10³<br>9<br><br>1.57 |
| Ch21_7 / Ch1 | 24 t21, PCR Enrichment<br>Ch1_1<br>Ch21_7<br>Ch21_7 / Ch1_1<br>24 t21, cf plasma DNA<br>Ch1_1<br>Ch21_7 | 1<br><br>24 × 5 × 10³<br>207 | 606 × 10³<br>9 × 5 × 10³<br><br>131 | 606 × 10³<br>0.33<br><br>0.63 |
| Ch1 | 24 t21, cf plasma DNA<br>Ch1_1 | 7 × 10³<br>199 | | |
| T21 Cellular DNA | T21 Cellular gDNA, PCR Enrichment<br>Ch1_1<br>Ch21_7 / Ch1_1<br>T21 Cellular gDNA<br>Ch1_1<br>Ch21_7 | 2850 × 10³<br><br>46 × 2 × 10³ | 511 × 10³<br><br>50 × 2 × 10³ | 0.20<br><br>1.09 |

Figure 10

| | PCR Size (bp) | BLAST |
|---|---|---|
| [S] chr21:40,372,644-40,372,655 | | |
| 5_150_40372655_F TGCCATCGTAGTTCAGCGTA | 153 | Ch21 |
| 5_150_40372655_R TTGGACCACAGCTCAGAGG | | Ch21 |

```
  1 CAAGACACAAGCAGGAGAGGACAAAAGCCAATGCAGCCTTA TGCCATCGTAGTTCAGCGTA
 61 GCGGAAGTTCGGTTTGGCTTCTTCCGGCAGCCCTGGTTGCACACTGTCCAATCTCAGCTCA
121 TACCAGGTGGCTTCCTGCAGGTCATACAGGATGTAGGACTGGAGAGACAAGG CCTCTGA
       TGCATCGTAGTTCAGCGTAAGCAAGTGGAGCT    20% of reads
       TGGGACCACAGCTCAGAGGAGGACTCCAAGTC    18% of reads
       Library_24103_5_150
181 GCTCTGTCCTCCAG CTCTGAGCTGTGGTCCAAGGGGCT
```

Figure 12

| Primer pair 18 | Sequence (5'->3') | Strand on template | Length | Start | Stop | Tm | GC% |
|---|---|---|---|---|---|---|---|
| Forward | TGAAGCCCGGGGAGGTTCCCT | Plus | 20 | 226632815 | 226632834 | 59.16 | 65.00% |
| Reverse | TCCAGGCTGTGTGCCGTCCC | Minus | 20 | 226632954 | 226632935 | 60.47 | 70.00% |
| Internal oligo | | Plus | | | | | |
| Product length | 140 | | | | | | |

Figure 15

| Ch21 Regions | Primer | ID of Plasma DNA | | | | | Genomic DNA |
|---|---|---|---|---|---|---|---|
| | | 24107 | 11215 | 11205 | 24101 | 24102 | Non-Pregnant |
| Region A (7 Clusters) | A2 | ND | ND | ND | ND | ND | ND |
| | A28 | ND | ND | ND | ND | ND | ND |
| | A7 | 5.87 | 5.21 | 4.83 | 5.09 | 2.97 | 10.54 |
| | A18 | 2.71 | 1.87 | 3.1 | 2.68 | 4.74 | 9.31 |
| | A73 | 4.21 | 3.29 | 3.99 | 2.22 | 1.85 | 7.96 |
| | A25 | 1.44 | ND | ND | 1.4 | ND | 2.49 |
| | A72 | 1.94 | 1.47 | ND | 1.7 | 2.34 | 1.86 |
| Region B (6 Clusters) | B19 | ND | ND | ND | ND | ND | ND |
| | B54 | 15.15 | 6.02 | 15.6 | 11.33 | 10.87 | 25.22 |
| | B16 | 3.83 | 2.57 | No Data | 1.9 | 2.59 | 13.14 |
| | B7 | 4.77 | 2.57 | 3.47 | 17.29 | 3.93 | 4.8 |
| | B32 | ND | ND | 1.47 | ND | ND | 3.24 |
| | B34 | ND | ND | ND | ND | ND | 2.09 |
| Region C (8 Clusters) | C55 | 12.36 | 8.59 | 15.27 | 6.82 | 10.06 | 25.74 |
| | C72 | 8.57 | 5.87 | 10.97 | 7.38 | 8.41 | 16.40 |
| | C74 | 9.09 | 5.61 | 6.74 | 5.52 | 5.69 | 15.51 |
| | C19 | 8.34 | 4.97 | 7.27 | 6.27 | 6.98 | 11.06 |
| | C29 | 11.14 | 4.67 | 6.47 | 6.69 | 6.6 | 7.83 |
| | C1 | 3.87 | 2.17 | 3.59 | 3.62 | 4.48 | 4.69 |
| | C6 | ND | 1.96 | 2.55 | ND | 2.12 | 3.37 |
| | C58 | ND | ND | ND | ND | ND | 0.97 |

ND: Not Detectable    Conc. ng / ul

Figure 17

| Primer | ID cf Plasma DNA ||||||| Genomic DNA |
| --- | --- | --- | --- | --- | --- | --- | --- | --- |
| | 24107 | 11215 | 11205 | 24101 | 24102 | 24103 | 24109 | Non-Pregnant |
| Ch1_1_150 | 15.54 | 14.93 | 14.13 | 10.99 | 18.28 | 17.15 | 13.75 | 30.28 |
| Ch1_2_150 | 15.15 | 9.94 | 12.6 | 7.69 | 6.98 | 9.69 | 8.65 | 19.44 |
| Ch2_1-150 | 5.84 | 5.92 | 5.51 | 3.94 | 5.86 | 6.4 | 3.79 | 12.66 |
| Ch2_2_150 | 3.45 | 2.84 | 2.96 | 2.63 | 2.94 | 3.24 | 2.04 | 7.63 |
| Ch3_1_150 | 6.12 | 4.18 | 6.91 | 4.1 | 5.73 | 5.14 | 4.22 | 11.44 |

Conc. ng / ul

Figure 18

| Chromosome Walk | Sequencing Data |
|---|---|
| 76% Amplification (16 / 21) | 100% Amplification (7 / 7) |
| Ch 21 Enrichment | |
| | 100% Amplification (5 / 5) |
| Ref Ch1, 2, 3 Enrichment | |

Figure 21
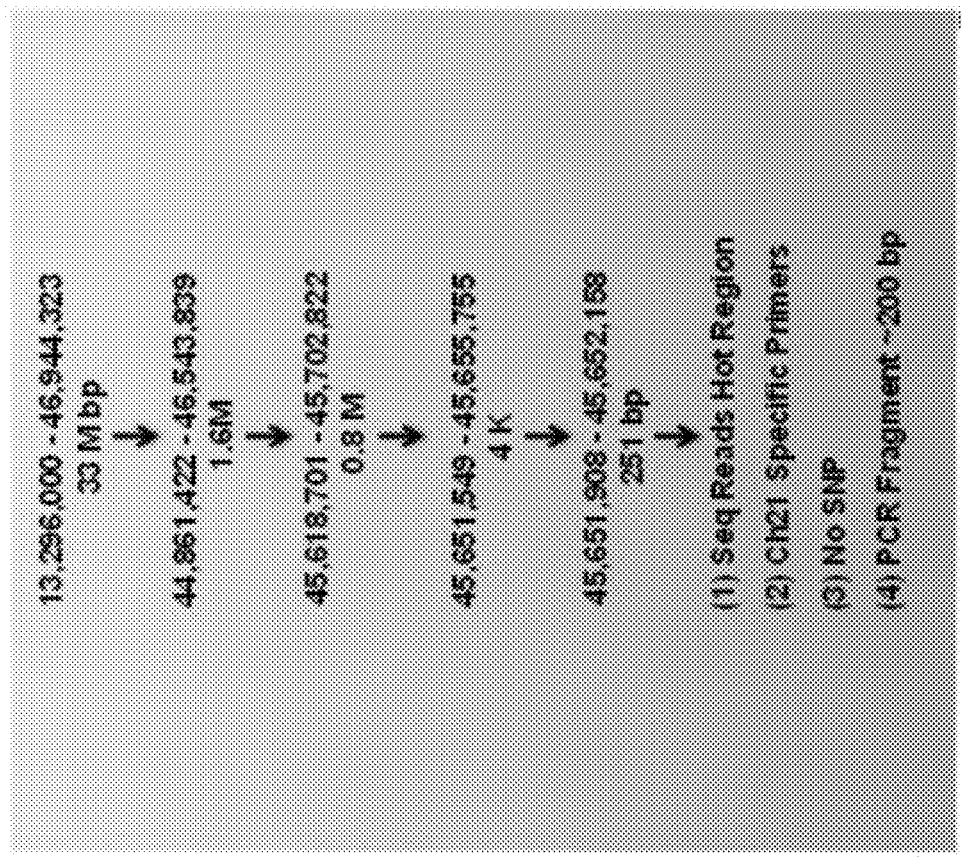
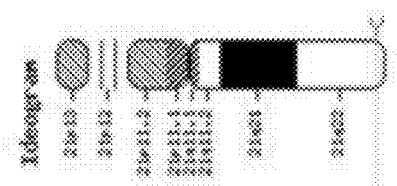

METHODS OF FETAL ABNORMALITY DETECTION

CROSS-REFERENCE

This application is a continuation of U.S. patent application Ser. No. 13/012,222, filed Jan. 24, 2011, which claims the benefit of U.S. Provisional Application No. 61/297,755, filed Jan. 23, 2010, each of which application is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jan. 25, 2012, is named 32477692.txt and is 27,793 bytes in size.

BACKGROUND OF THE INVENTION

Massively parallel sequencing techniques are used for detection of fetal aneuploidy from samples that comprise fetal and maternal nucleic acids. Fetal DNA often constitutes less than 10% of the total DNA in a sample, for example, a maternal cell-free plasma sample. Sequencing a large number of polynucleotides to generate sufficient data for fetal aneuploidy detection can be expensive. Methods for randomly enriching fetal nucleic acids in cell-free maternal sample have been described, including enriching nucleic acids based on size, formaldehyde treatment, methylation status, or hybridization to oligonucleotide arrays. There is a need for a means of selectively enriching non-random fetal and maternal polynucleotide sequences in a way that facilitates aneuploidy detection by massively parallel sequencing techniques and increases the sensitivity of aneuploidy detection.

SUMMARY OF THE INVENTION

In one aspect, a method for determining the presence or absence of fetal aneuploidy is provided comprising a) selectively enriching non-random polynucleotide sequences of genomic DNA from a cell-free DNA sample; b) sequencing said enriched polynucleotide sequences; c) enumerating sequence reads from said sequencing step; and d) determining the presence or absence of fetal aneuploidy based on said enumerating. In one embodiment, said selectively enriching comprises performing PCR. In another embodiment, said selectively enriching comprises linear amplification. In another embodiment, said selectively enriching comprises enriching at least 1, 5, 10, 50, 100, or 1000 non-random polynucleotide sequences from a first chromosome. In another embodiment, said selectively enriching comprises enriching at least 1, 10, or 100 polynucleotide sequences from one or more regions of a first chromosome, wherein each region is up to 50 kb. In another embodiment, said non-random polynucleotide sequences comprise sequences that are sequenced at a rate of greater than 5-fold than other sequences on the same chromosome. In another embodiment, said non-random polynucleotide sequences each comprise about 50-1000 bases. In another embodiment, said cell-free DNA sample is a maternal sample. In another embodiment, said maternal sample is a maternal blood sample. In another embodiment, said maternal sample comprises fetal and maternal cell-free DNA. In another embodiment, said cell-free DNA is from a plurality of different individuals. In another embodiment, said sequencing comprises Sanger sequencing, sequencing-by-synthesis, or massively parallel sequencing.

In another embodiment, said aneuploidy is trisomy 21, trisomy 18, or trisomy 13. In another embodiment, said aneuploidy is suspected or determined when the number of enumerated sequences is greater than a predetermined amount. In another embodiment, said predetermined amount is based on estimated amount of DNA in said cell-free DNA sample. In another embodiment, said predetermined amount is based on the amount of enumerated sequences from a control region.

In another aspect, a method is provided comprising: a) providing oligonucleotides that specifically hybridize to one or more polynucleotide sequences from a polynucleotide template, wherein said one or more polynucleotide sequences comprise sequences that are sequenced at rate greater than 5-fold than other sequences from the polynucleotide template; b) selectively enriching said one or more polynucleotide sequences; and c) optionally sequencing said enriched one or more polynucleotide sequences.

In another embodiment, each of said oligonucleotides has a substantially similar thermal profile. In another embodiment, said polynucleotide sequences each comprise about 50-1000 bases. In another embodiment, said polynucleotide sequences are from a cell-free DNA sample. In another embodiment, said polynucleotide sequences are from a maternal sample. In another embodiment, said maternal sample is a maternal blood sample. In another embodiment, said maternal sample comprises fetal and maternal cell-free DNA. In another embodiment, said polynucleotide template is a chromosome suspected of being aneuploid. In another embodiment, said polynucleotide template is chromosome 21. In another embodiment, the polynucleotide template is a chromosome not suspected of being aneuploid. In another embodiment, said polynucleotide template is chromosome 1, 2, 3, 4, 5, 6, 7, 8, 9, 10, 11, 12, 14, 15, 16, 17, 19, 20, or 22.

In another embodiment, said rate is at least 10 or 50-fold. In another embodiment, there are at least 7, 10, 17, or 27 sequence reads for the sequences that were sequenced at a higher frequency rate. In another embodiment, said selectively enriching comprises performing PCR. In another embodiment, said selectively enriching comprises linear amplification. In another embodiment, said selectively enriching comprises enriching at least 1, 5, 10, 50, 100, or 1000 non-random polynucleotide sequences from a first chromosome. In another embodiment, said selectively enriching comprises enriching at least 1, 10, or 100 polynucleotide sequences from one or more regions of a first chromosome, wherein each region is up to 50 kb. In another embodiment, said sequencing comprises Sanger sequencing, sequencing-by-synthesis, or massively parallel sequencing.

In another embodiment, the method further comprises a step of determining the presence of absence of fetal aneuploidy based on said sequencing In another aspect, a method for identifying polynucleotide sequences for enrichment in a polynucleotide template is provided comprising: a) sequencing a plurality of polynucleotide sequences from the polynucleotide template; b) enumerating sequenced polynucleotide sequences; and c) identifying one or more sequenced polynucleotide sequences that are sequenced or that have a coverage rate at least 5-fold greater than a second set of polynucleotide sequences.

In one embodiment, said polynucleotide sequences are from a cell-free DNA sample. In another embodiment, said polynucleotide sequences are from a maternal sample. In another embodiment, said sequencing coverage rate is at least 10- or 50-fold. In another embodiment, there are at least 7, 10, 17, or 27 reads for the polynucleotide sequences that were sequenced at a higher frequency rate.

In another embodiment, said identified polynucleotide sequences are used to determine the presence or absence of fetal aneuploidy.

In another aspect, a kit comprising a set of oligonucleotides that selectively amplify one or more regions of a chromosome is provided, wherein each of said regions is sequenced at a rate of greater than 5-fold than other regions of the chromosome.

In one embodiment, each of said oligonucleotides in the kit is part of an oligonucleotide pair. In another embodiment, said set of oligonucleotides comprises at least 100 oligonucleotides. In another embodiment, an oligonucleotide in each oligonucleotide pair comprises sequence identical to sequence in an oligonucleotide in the other pairs and sequence unique to that individual oligonucleotide.

In another aspect, a method for sequencing cell-free DNA from a maternal sample is provided comprising: a) obtaining a maternal sample comprising cell-free DNA, b) enriching sequences that are representative of a plurality of up to 50 kb regions of a chromosome, or enriching sequences that are sequenced at a rate of at least 5-fold greater than other sequences using an Illumina Genome Analyzer sequencer, and c) sequencing said enriched sequences of cell-free DNA.

In one embodiment, said sequencing comprises sequencing-by-synthesis. In another embodiment, said method further comprises bridge amplification. In another embodiment, said sequencing comprises Sanger sequencing. In another embodiment, said sequencing comprises single molecule sequencing. In another embodiment, said sequencing comprises pyrosequencing. In another embodiment, said sequencing comprises a four-color sequencing-by-ligation scheme. In another embodiment, said sequenced enriched sequences are used to determine the presence or absence of fetal aneuploidy. In another aspect, one or more unique isolated genomic DNA sequences are provided, wherein said genomic DNA sequences comprise regions that are sequenced at a rate greater than 500% than other regions of genomic DNA. In another embodiment, the isolated genomic DNA are sequenced by a method comprising bridge amplification, Sanger sequencing, single molecule sequencing, pyrosequencing, or a four-color sequencing by ligation scheme. In another embodiment, the isolated genomic regions comprise at least 100, 1000, or 10,000 different sequences. In another embodiment, the regions are present at a rate greater than 50-fold, 100-fold, 20-fold. In another embodiment, the sequence is a single amplicon.

In another aspect, a set of one or more oligonucleotides are provided that selectively hybridize to one or more unique genomic DNA sequences, wherein said genomic DNA sequences comprise regions that are sequenced at a rate greater than 500% than other regions of genomic DNA. In one embodiment, the oligonucleotides hybridize to the sequences under mild hybridization conditions. In another embodiment, the oligonucleotides have similar thermal profiles.

In another aspect, a method is provided comprising: a) amplifying one or more polynucleotide sequences with a first set of oligonucleotide pairs; b) amplifying the product of a) with a second set of oligonucleotides pairs; and c) amplifying the product of b) with a third set of oligonucleotide pairs. In one embodiment, the first set of oligonucleotide pairs comprises sequence that distinguishes polynucleotides in one sample from polynucleotides in another sample. In another embodiment, said first set of oligonucleotide pairs comprises sequence that distinguishes polynucleotides in one sample from polynucleotides in another sample and sequence that extends the length of the product. In another embodiment, said polynucleotide sequences are enriched sequences.

In another aspect, a method for labeling enriched polynucleotides in two or more samples that allows identification of which sample the polynucleotide originated is provided, comprising: a) amplifying one or more polynucleotide sequences in two or more samples with a first set of oligonucleotide pairs, wherein the first set of oligonucleotide pairs comprises sequence that distinguishes polynucleotides from one sample from polynucleotides in another sample; b) amplifying the product of a) with a second set of oligonucleotides pairs; and c) amplifying the product of b) with a third set of oligonucleotide pairs.

In another aspect, a kit is provided comprising a) a first set of oligonucleotide primer pairs comprising: sequence that selectively hybridizes to a first set of genomic DNA sequences and sequence in-common amongst each of the first set of oligonucleotide primer pairs, b) a second set of oligonucleotide primer pairs with sequence that selectively hybridizes to the common sequence of the first set of oligonucleotide primer pairs and sequence common to the second set of oligonucleotide pairs, and c) a third set of oligonucleotide primer pairs with sequence that selectively hybridizes to the common sequence of the second set of oligonucleotide pairs. In one embodiment, the common region in the first set of primers comprises sequence that distinguishes polynucleotides in one sample from polynucleotides in another sample. In another embodiment, the common region in the first set of primers comprises sequence that distinguishes polynucleotides in one sample from polynucleotides in another sample and sequence that extends the length of the product.

In another aspect, a kit is provided comprising: a first set of primer pairs that selectively amplifies a set of genomic sequences to create a first set of amplification products, a second set of primer pair that selectively amplifies the first set of amplification products, and a third set of primer pairs that selectively amplifies the second set of amplification products.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 illustrates results of amplification of chromosome 21 with different primer pairs.

FIG. 5 illustrates simplex PCR amplification Bioanalyzer results.

FIG. 10 illustrates Illumina GA sequencing analysis. FIG. 10 discloses SEQ ID NOS:9-10 and 96-98, respectively.

FIG. 12 illustrates a primer pair (SEQ ID NOS:42-43, respectively, in order of appearance) designed for use in PCR amplification.

FIG. 15 illustrates enrichment of regions of chromosome 21 using the "chromosome walk" sequence selection method.

FIG. 17 illustrates enrichment of sequences from reference chromosomes 1, 2, and 3.

FIG. 18 illustrates chromosome amplification rates of sequences selected using the "chromosome walk" method or based on "hot spots."

FIG. 21 illustrates criteria used to select and amplify a "hot spot" region of chromosome 21.

FIG. 25 illustrates primers designed for amplifying sequence from a 251 bp segment of chromosome 21 (SEQ ID NO:133).

DETAILED DESCRIPTION OF THE INVENTION

Overview

Figure 1:
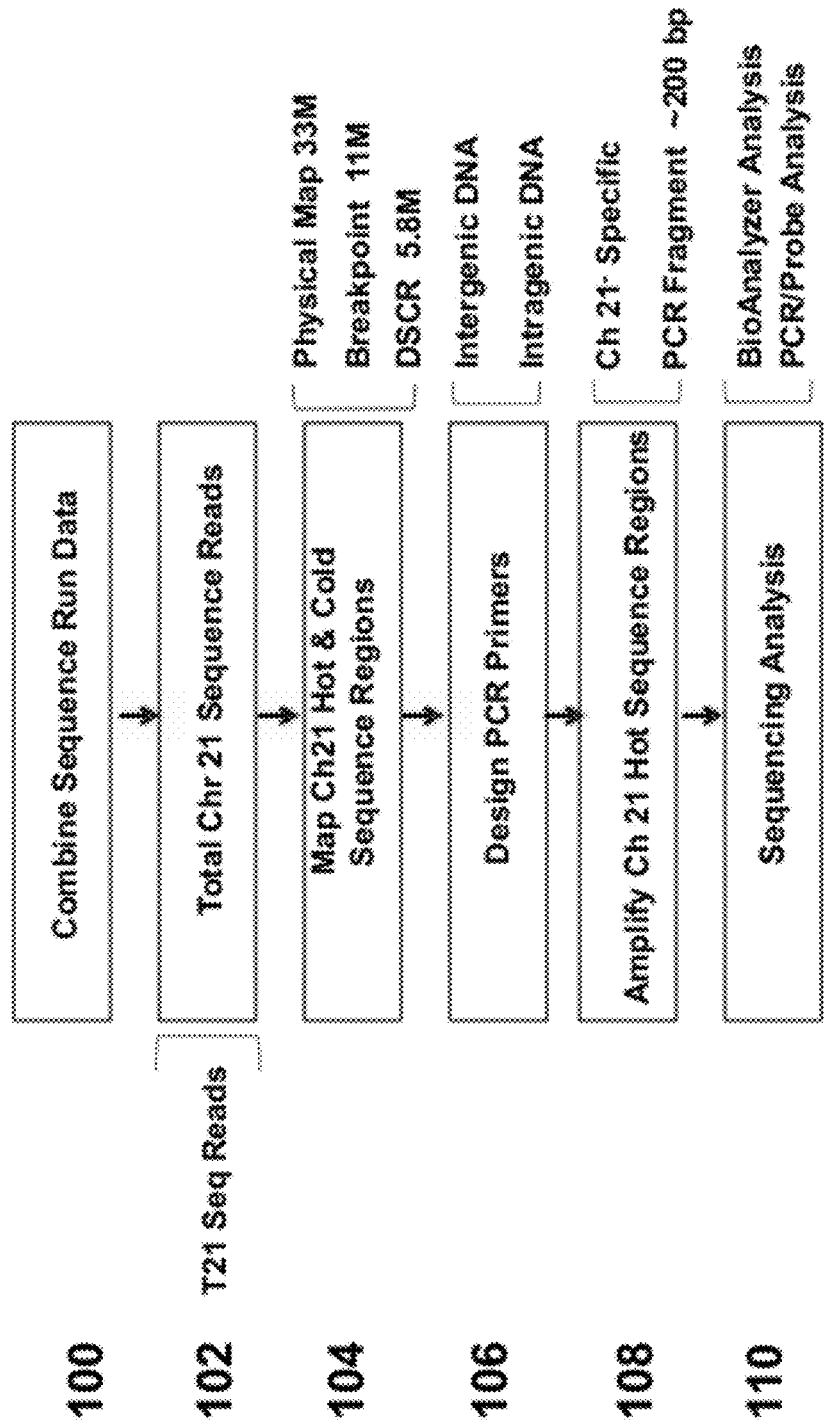
FIG. 1 illustrates a strategy for selecting sequences for enrichment based on "hot spots."

In one aspect, the provided invention includes methods for selecting non-random polynucleotide sequences for enrichment. The non-random sequences can be enriched from a maternal sample for use in detecting a fetal abnormality, for example, fetal aneuploidy. In one embodiment, the selection of non-random polynucleotide sequences for enrichment can be based on the frequency of sequence reads in a database of sequenced samples from one or more subjects. In another embodiment, the selection of polynucleotide sequences for enrichment can be based on the identification in a sample of sequences that can be amplified in one or more regions of a chromosome. The selection of polynucleotide sequences to enrich can be based on knowledge of regions of chromosomes that have a role in aneuploidy. The selective enrichment of sequences can comprise enriching both fetal and maternal polynucleotide sequences.

In another aspect, the provided invention includes methods for determining the presence or absence of a fetal abnormality comprising a step of enriching non-random polynucleotide sequences from a maternal sample. The non-random polynucleotide sequences can be both fetal and maternal polynucleotide sequences.

In another aspect, the provided invention comprises a kit comprising oligonucleotides for use in selectively enriching non-random polynucleotide sequences.

In another aspect, the provided invention includes methods for generating a library of enriched polynucleotide sequences. A library can be generated by the use of one or more amplification steps, which can introduce functional sequences in polynucleotide sequences that have been selectively enriched. For example, the amplification steps can introduce sequences that serve as hybridization sites for oligonucleotides for sequencing, sequences that identify that sample from which the library was generated, and/or sequences that serve to extend the length of the enriched polynucleotide sequences, for example, to facilitate sequencing analysis.

In one aspect, a method for determining the presence or absence of fetal aneuploidy is provided comprising selectively enriching non-random polynucleotide sequences (e.g., genomic DNA) from a cell-free nucleic acid (e.g., DNA or RNA) sample, sequencing said enriched polynucleotide sequences, enumerating sequence reads from said sequencing step, and determining the presence or absence of fetal aneuploidy based on said enumerating.

The selectively enriching step can comprise amplifying nucleic acids. Amplification can comprise performing a polymerase chain reaction (PCR) on a sample of nucleic acids. PCR techniques that can be used include, for example, digital PCR (dPCR), quantitative PCR (qPCR) or real-time PCR (e.g., TaqMan PCR; Applied Biosystems), reverse-transcription PCR (RT-PCR), allele-specific PCR, amplified fragment length polymorphism PCR (AFLP PCR), colony PCR, Hot Start PCR, in situ PCR (ISH PCR), inverse PCR (IPCR), long PCR, multiplex PCR, or nested PCR. Amplification can be linear amplification, wherein the number of copies of a nucleic acid increases at a linear rate in a reaction.

The selectively enriching step can comprise a hybridization step. The hybridization can occur on a solid support.

Selecting Sequences Based on "Hotspots"

Sequencing data can be analyzed to identify polynucleotide sequences to be selectively enriched. Some polynucleotide sequences from a sample comprising nucleic acids (e.g., genomic DNA) can be sequenced at a higher frequency than other polynucleotide sequences. These sequences may be more likely to be enriched by, for example, amplification methods. Identifying and enriching these polynucleotide sequences can reduce the number of nucleic acids that need to be analyzed to determine the presence or absence of fetal aneuploidy. This enrichment can reduce the cost of aneuploidy determination.

In one embodiment, the non-random polynucleotide sequences that are selectively enriched can comprise sequences that are sequenced at a frequency of greater than at least 2-, 3-, 4-, 5-, 6-, 7-, 8-, 9-, 10-, 15-, 20-, 25-, 30-, 40-, 50-, 60-, 70-, 80-, 90-, or 100-fold than other sequences on the same chromosome in a database of sequence information. The polynucleotide sequences that are sequenced at a higher frequency can be referred to as "hot-spots." The non-random polynucleotides that are selectively enriched can be selected from regions of a chromosome known to have a role in a disease, for example, Down syndrome. The sequencing rate data can be derived from a database of enumerated polynucleotide sequences, and the database of enumerated polynucleotide sequences can be generated from one or more samples comprising non-maternal samples, maternal samples, or samples from subjects that are pregnant, have been pregnant, or are suspected of being pregnant. The samples can be cell-free nucleic acid (e.g., DNA or RNA) samples. The subjects can be mammals, e.g., human, mouse, horse, cow, dog, or cat. The samples can contain maternal polynucleotide sequences and/or fetal polynucleotide sequences. The enumerated sequences can be derived from random, massively parallel sequencing of samples, e.g., as described in U.S. Patent Application Publication Nos. 20090029377 and 20090087847, or Fan H C et al. (2008) *PNAS* 105:16266-71, which are herein incorporated by reference in their entireties. Techniques for massively parallel sequencing of samples are described below.

Figure 22A:
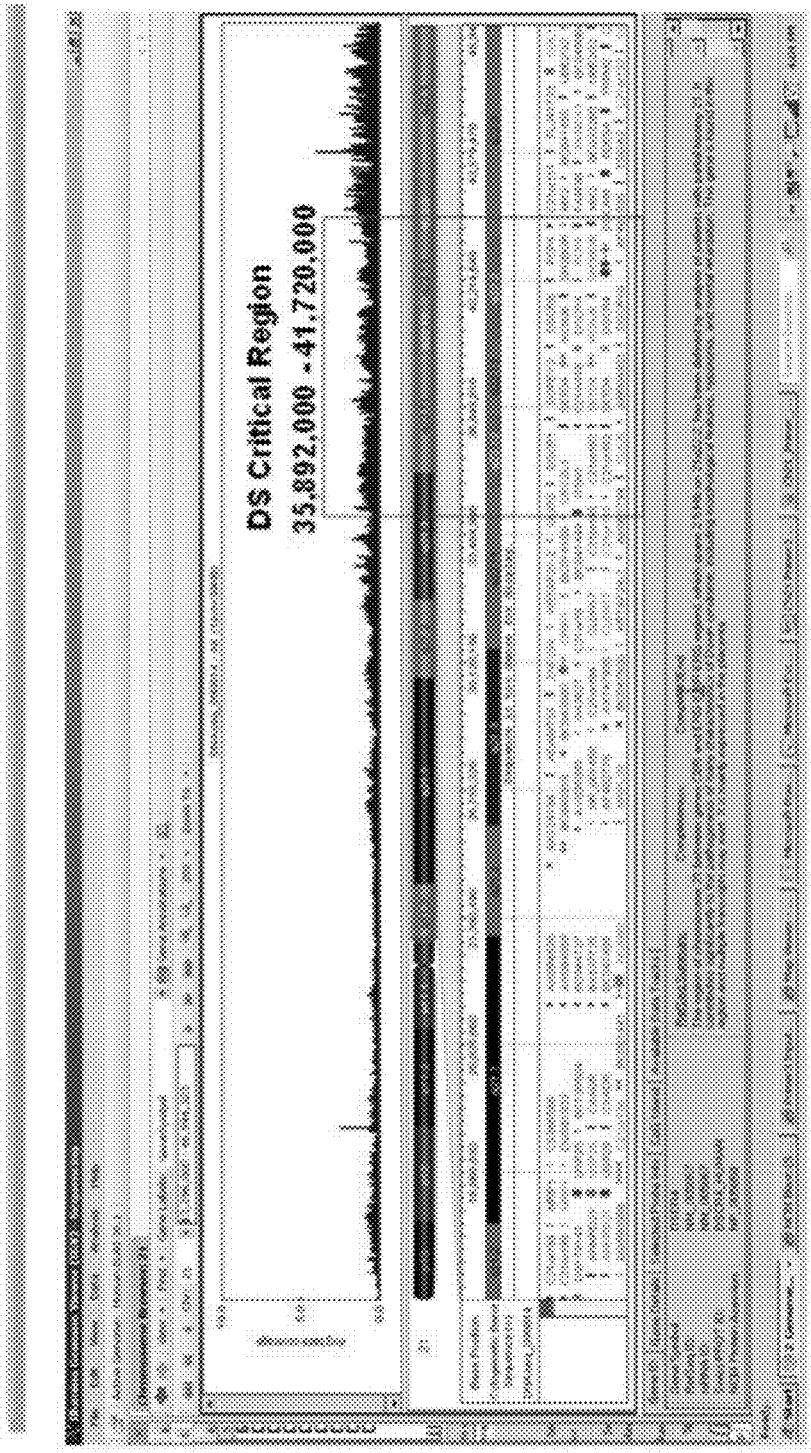
FIG. 22 highlights a Down syndrome critical region on a schematic of sequence reads that map to chromosome 21.
Figure 22B:
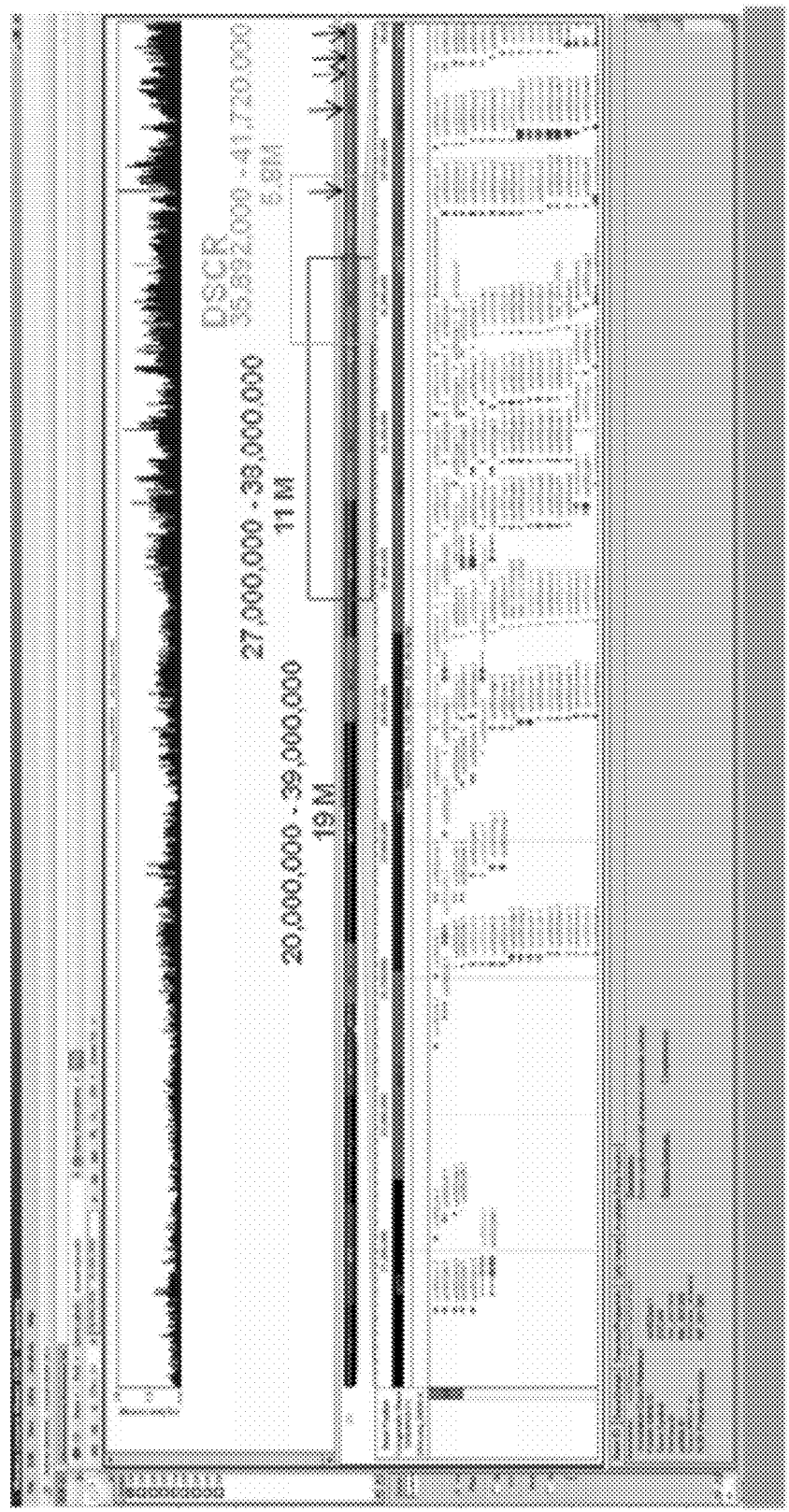
Figure 23:
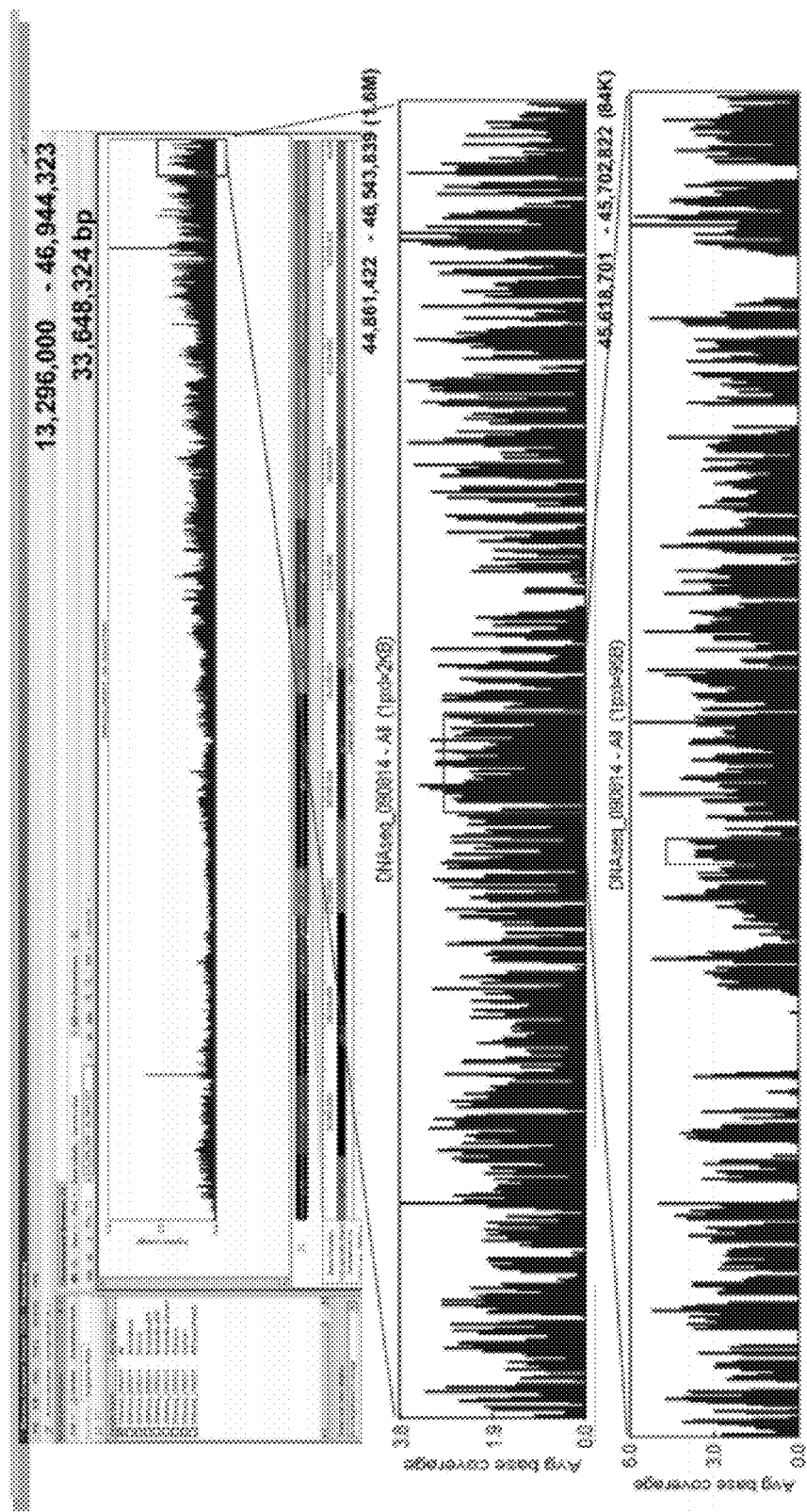
FIG. 23 magnifies regions of sequence read coverage on a schematic of chromosome 21.
Figure 24:
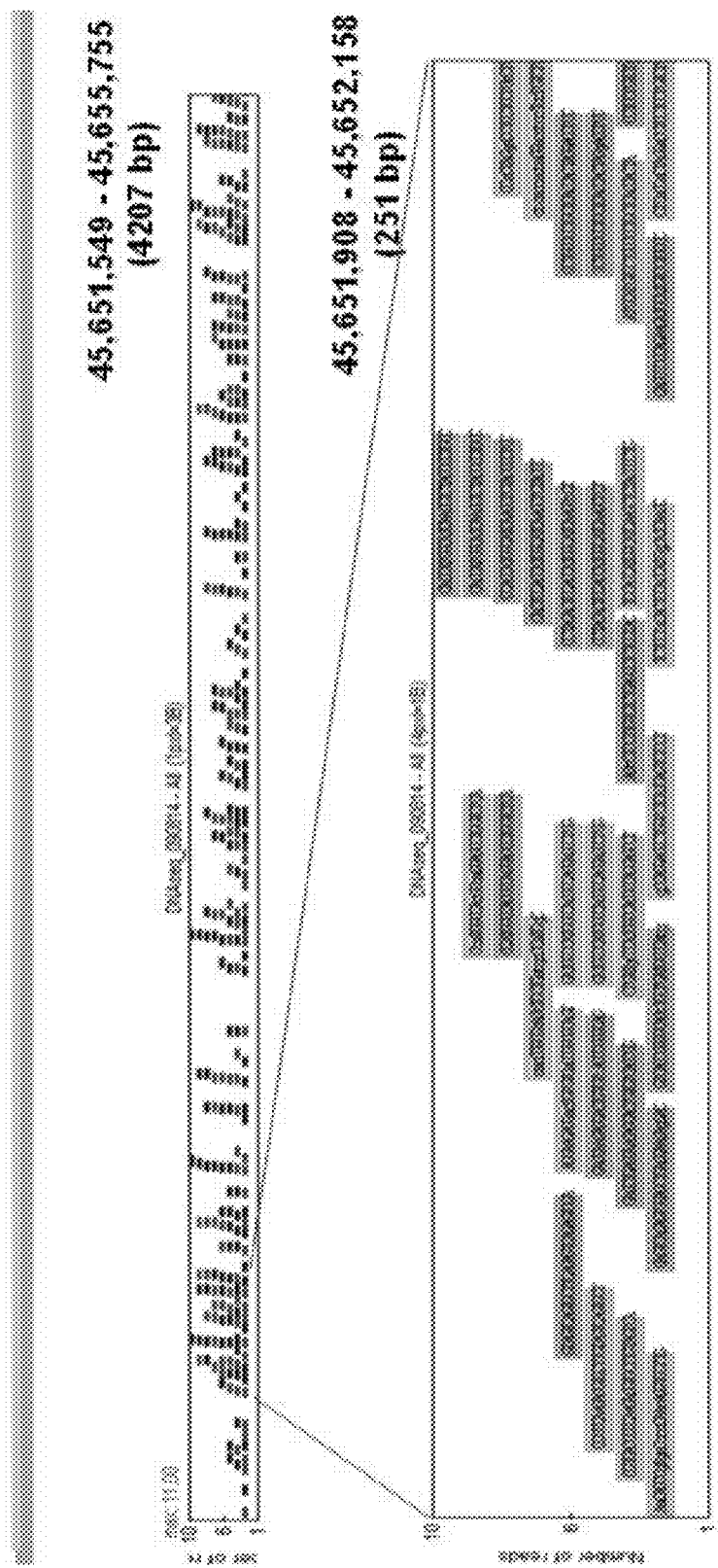
FIG. 24 illustrates sequences reads mapped on chromosome 21 (SEQ ID NOS:99-132, respectively, in order of appearance).

The database can comprise sequence information from samples from at least 1, 2, 3, 4, 5, 6, 7, 8, 9, 10, 11, 12, 13, 14, 15, 16, 17, 18, 19, 20, 21, 22, 23, 24, 25, 30, 40, 50, 60, 70, 80, 90, 100, 200, 300, 400, 500, 600, 700, 800, 900, 1000, 2000, 3000, 5000, 7500, 10,000, 100,000, or 1,000,000 different subjects. The data can be processed to indicate the overlap of individual polynucleotide sequences from the samples from the subjects (FIGS. 22-24). The database can indicate the frequency with which one or more nucleotides at a specific chromosome position is sequenced among the samples. The length of the sequence that can overlap can be at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 125, 150, 175, 200, 225, 250, 275, or 300 bases. The frequency of sequencing of one or more nucleotides at a first position of a chromosome can be compared to the frequency of sequencing of one or more other nucleotides at a second position on the chromosome to determine the fold frequency at which the first position was sequenced relative to the second position. The sequence (polynucleotide sequence or base) that is sequenced at a higher frequency can be sequenced at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 200, 300, 400, 500, 600, 700, 800, 900, 1000, 2000, 3000, 5000, 7500, 10,000, 100,000, or 1,000,000 times in one or more samples in the database.

In one embodiment, a method for identifying polynucleotide sequences for enrichment in a polynucleotide template is provided comprising sequencing a plurality of polynucleotide sequences from the polynucleotide template, enumerating sequenced polynucleotide sequences, and identifying one or more sequenced polynucleotide sequences that are sequenced or that have a coverage rate at least 5-fold greater than a second set of polynucleotide sequences.

In another aspect, one or more unique isolated genomic DNA sequences are provided, wherein said genomic DNA sequences comprise regions that are sequenced at a rate greater than 5-fold than other regions of genomic DNA. The isolated genomic sequences can comprise at least 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000 different sequences. Each isolated genomic sequence can be a single amplicon.

In another aspect, a set of one or more oligonucleotides that selectively hybridize to the isolated sequences is provided. The oligonucleotides can hybridize to the sequences under mild hybridization conditions. The oligonucleotides can have similar thermal profiles.

In one embodiment, the non-random sequences to be selectively enriched are identified based on the number of times they are sequenced in a database of sequence information, independent of the rate of sequencing of a second set of sequences. For example, the sequences to be selectively enriched can be those that are sequenced at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 200, 300, 400, 500, 600, 700, 800, 900, 1000, 2000, 3000, 5000, 7500, 10,000, 100,000, or 1,000,000 times in one or more samples in the database.

The number of non-random polynucleotide sequences that can be selectively enriched in a sample can be at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 150, 200, 250, 300, 400, 500, 600, 700, 750, 800, 900, or 1000. The size of the non-random polynucleotide sequences to be selectively enriched can comprise about 10-1000, 10-500, 10-260, 10-260, 10-200, 50-150, or 50-100 bases or bp, or at least 10, 15, 20, 25, 30, 35, 40, 45, 50, 55, 60, 66, 70, 75, 80, 85, 90, 95, 100, 110, 120, 130, 140, 150, 160, 170, 180, 190, 200, 210, 220, 230, 240, 250, 260, 270, 280, 290, 300, 400, 500, 600, 700, 800, 900, or 1000 bases or bp.

The selective enrichment step can comprise designing oligonucleotides (primers) that hybridize specifically to polynucleotide sequences that are sequenced at a higher frequency than other sequences on a chromosome or are sequenced a certain number of times. A program, for example, Basic Local Alignment Search Tool (BLAST), can be used to design oligonucleotides that hybridize to sequence specific to one chromosome or region. The oligonucleotide primers can be manually designed by a user, e.g., using known genome or chromosome sequence template as a guide. A computer can be used to design the oligonucleotides. The oligonucleotides can be designed to avoid hybridizing to sequence with one or more polymorphisms, e.g., single nucleotide polymorphisms (SNPs).

One or more oligonucleotide pairs can be generated to hybridize specifically to one or more polynucleotide sequences; the oligonucleotide pairs can be used in amplification reactions, e.g., a PCR technique described above, to selectively enrich sequences. In one embodiment, the oligonucleotides or oligonucleotide pairs can be provided in a kit. A set of oligonucleotides can be generated wherein each oligonucleotide has a similar thermal profile (e.g., $T_m$). A set of oligonucleotides can comprise at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 oligonucleotide pairs. An oligonucleotide pair can be a pair of oligonucleotides that can hybridize to and amplify a sequence in a PCR. Each of the pairs of oligonucleotides can comprise sequence identical to sequence in all the other oligonucleotide pairs and sequence unique to that individual oligonucleotide pair.

In another aspect, a kit comprising a set of oligonucleotides that selectively hybridize and/or used to amplify one or more regions of a chromosome is provided, wherein each of said regions is sequenced at a rate of greater than 5-fold than other regions of the chromosome. The oligonucleotides can have the properties of the oligonucleotides described above.

Selecting Sequences Based on "Chromosome Walk"

In another embodiment, the selective enriching of non-random polynucleotide sequences can comprise identifying for enrichment and/or enriching at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 polynucleotide sequences from one or more regions of a first chromosome. The length of a region can be at least, or up to, 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000, or 10,000 kb. The number of regions from which sequences can be enriched can be at least 1, 2, 3, 4, 5, 6, 7, 8, 9, or 10. The selection of polynucleotide sequences to be enriched can be independent of the rate at which polynucleotides are sequenced in other samples. The polynucleotide sequences to be enriched can be clustered in a region, wherein the cluster can comprise about 1000-8000 bp, 1000-7000 bp, 1000-6000 bp, 1000-5000 bp, 1000-4000 bp, 1000-3000 bp, 1000-2000 bp, 4000-8000 bp, 5000-8000 bp, 6000-8000 bp, or 7000-8000 bp. There can be at least 1, 2, 3, 4, 5, 6, 7, 8, 9, or 10 clusters per region (e.g., per 50 kb region). The regions can be selected based on knowledge of a role for the region in a disease, for example, Down syndrome. Some polynucleotide sequences selected using this technique can be enriched (e.g., amplified) in practice, whereas some of the polynucleotide sequences selected using this technique may not be enriched (e.g., amplified) in practice. The polynucleotide sequences that are enriched using this identification technique can be used for subsequent enumeration and aneuploidy detection.

Oligonucleotide (primers) can be designed that hybridize specifically to polynucleotide sequences within a region (e.g., 50 kb). The oligonucleotide (primer) design can be automated to select sequences within a region (e.g., 50 kb) for enrichment using assembled chromosome sequence as a template for design. No prior knowledge of the level of sequenced polynucleotide sequences in other samples (e.g., in a database sequence information) is necessary to select the sequences for enrichment. PRIMER-BLAST (from NCBI open/public software) can be used to design oligonucleotides that specifically hybridize to sequences on one chromosome. The oligonucleotides can be designed to avoid hybridizing with sequences that contains one or more polymorphisms, e.g., a single nucleotide polymorphism (SNP). One or more oligonucleotide pairs can be generated to hybridize specifically to one or more polynucleotide sequences; the oligonucleotide pairs can be used in amplification reactions, e.g., using a PCR technique described above. A set of oligonucleotides can be generated wherein each oligonucleotide has a similar thermal profile (e.g., $T_m$). The set of oligonucleotides can comprise at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 oligonucleotide pairs. In one embodiment, a kit is provided comprising oligonucleotide pairs that can hybridize to specific polynucleotide sequences within a region (e.g., 50 kb). Each of the pairs of oligonucleotides can comprises sequence identical to sequence in all the other oligonucleotide pairs and sequence unique to that individual oligonucleotide pair.

Samples

The sample from which the non-random polynucleotide sequences are to be selectively enriched can be a maternal sample. Maternal samples that can be used in the methods of the provided invention include, for example, whole blood, serum, plasma, sweat, tears, ear flow, sputum, lymph, bone marrow suspension, lymph, urine, saliva, semen, sweat, vaginal flow, feces, transcervical lavage, cerebrospinal fluid, brain fluid, ascites, milk, or secretions of the respiratory, intestinal and genitourinary tracts. A sample can be from a processed blood sample, for example, a buffy coat sample. A buffy coat sample is an anticoagulated blood sample that forms after density gradient centrifugation of whole blood. A buffy coat sample contains, e.g., maternal nucleated cells, e.g., peripheral blood mononuclear cells (PBMCs). In one embodiment, a sample comprises fetal cells (e.g., fetal nucleated red blood cells (fnRBCs) or trophoblasts) and maternal cells.

A cell-free nucleic acid (e.g., DNA or RNA) sample can be a maternal sample, for example, serum or plasma. Methods for generating serum or plasma and methods for extracting nucleic acids are known in the art. A cell-free sample can comprise fetal and maternal cell-free nucleic acid, for example, DNA or RNA. A cell-free DNA sample can be from a plurality of different subjects. Samples used for generation of a database of sequenced polynucleotides can be cell-free nucleic acid samples.

Sequencing Methods

Applicable nucleic acid sequencing methods that can be used in the methods of the provided invention include, e.g., multi-parallel sequencing, massively parallel sequencing, sequencing-by-synthesis, ultra-deep sequencing, shot-gun sequencing, and Sanger sequencing, e.g., using labeled terminators or primers and gel separation in slab or capillary. These sequencing methods have been described previously. For example, a description of shotgun sequencing can be found in Fan et al. (2008) *PNAS* 105:16266-16271. Sanger sequencing methods are described in Sambrook et al., (2001) Molecular Cloning, Third Edition, Cold Spring Harbor Laboratory Press. Other DNA sequencing techniques can include sequencing-by-synthesis using reversibly terminated labeled nucleotides, pyrosequencing, 454 sequencing, allele specific hybridization to a library of labeled oligonucleotide probes, sequencing by synthesis using allele specific hybridization to a library of labeled clones followed by ligation, real time monitoring of the incorporation of labeled nucleotides during a polymerization step, polony sequencing, and SOLiD sequencing.

Sequencing methods are described in more detail below. A sequencing technology that can be used in the methods of the provided invention is SOLEXA sequencing (Illumina) SOLEXA sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another sequencing technique that can be used in the methods of the provided invention includes, for example, Helicos True Single Molecule Sequencing (tSMS) (Harris T. D. et al. (2008) *Science* 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm². The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step.

Another example of a DNA sequencing technique that can be used in the methods of the provided invention is 454 sequencing (Roche; Margulies, M. et al. (2005) *Nature* 437: 376-380). 454 sequencing involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated.

Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used in the methods of the provided invention is SOLiD technology (Applied Biosystems). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide.

The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a sequencing technology that can be used in the methods of the provided invention includes the single molecule, real-time (SMRT™) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off Detection of the corresponding fluorescence of the dye indicates which base was incorporated. The process is repeated.

Another example of a sequencing technique that can be used is the methods of the provided invention is nanopore sequencing (Soni G V and Meller A. (2007) *Clin Chem* 53:1996-2001). A nanopore is a small hole, of the order of 1 nanometer in diameter Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using a chemical-sensitive field effect transistor (chemFET) array to sequence DNA (e.g., as described in U.S. Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

The sequencing technique used in the methods of the provided invention can generate at least 1000 reads per run, at least 10,000 reads per run, at least 100,000 reads per run, at least 500,000 reads per run, or at least 1,000,000 reads per run.

The sequencing technique used in the methods of the provided invention can generate about 30 bp, about 40 bp, about 50 bp, about 60 bp, about 70 bp, about 80 bp, about 90 bp, about 100 bp, about 110, about 120 bp per read, about 150 bp, about 200 bp, about 250 bp, about 300 bp, about 350 bp, about 400 bp, about 450 bp, about 500 bp, about 550 bp, or about 600 bp per read.

The sequencing technique used in the methods of the provided invention can generate at least 30, 40, 50, 60, 70, 80, 90, 100, 110, 120, 150, 200, 250, 300, 350, 400, 450, 500, 550, or 600 bp per read.

In another aspect, a method for sequencing cell-free DNA from a maternal sample is provided comprising obtaining a maternal sample comprising cell-free DNA, enriching sequences that are representative of one or more 50 kb regions of a chromosome, or enriching sequences that are sequenced at a rate of at least 2-fold greater than other sequences, using an Illumina sequencer (e.g., Illumina Genome Analyzer IIx) and sequencing said enriched sequences of cell-free DNA.
Aneuploidy The non-random sequences to be selectively enriched can include those on a chromosome suspected of being aneuploid in a fetus and/or on a chromosome suspected of being euploid in a fetus. Polynucleotide sequences from chromosome 1, 2, 3, 4, 5, 6, 7, 8, 9, 10, 11, 12, 13, 14, 15, 16, 17, 18, 19, 20, 21, 22, X, or Y can be selectively enriched. Chromosomes suspected of being aneuploid in a fetus can include chromosome 1, 2, 3, 4, 5, 6, 7, 8, 9, 10, 11, 12, 13, 14, 15, 16, 17, 18, 19, 20, 21, 22, X, or Y. Chromosomes suspected of being euploid in a fetus can include chromosome 1, 2, 3, 4, 5, 6, 7, 8, 9, 10, 11, 12, 13, 14, 15, 16, 17, 18, 19, 20, 21, 22, X, or Y.

The methods of the provided invention can be used to detect aneuploidy. Aneuploidy is a state where there is an abnormal number of chromosome(s), or parts of a chromosome. Aneuploidy can include, for example, monosomy, partial monosomy, trisomy, partial trisomy, tetrasomy, and pentasomy. Examples of aneuploidy that can be detected include Angelman syndrome (15q11.2-q13), cri-du-chat syndrome (5p-), DiGeorge syndrome and Velo-cardiofacial syndrome (22q11.2), Miller-Dieker syndrome (17 p13.3), Prader-Willi syndrome (15q11.2-q13), retinoblastoma (13q14), Smith-Magenis syndrome (17 p11.2), trisomy 13 (Patau syndrome), trisomy 16, trisomy 18 (Edward syndrome), trisomy 21 (Down syndrome), triploidy, Williams syndrome (7q 11.23), and Wolf-Hirschhom syndrome (4p-). Examples of sex chromosome abnormalities that can be detected by methods described herein include, but are not limited to, Kallman syndrome (Xp22.3), steroid sulfate deficiency (STS) (Xp22.3), X-linked ichthyosis (Xp22.3), Klinefelter syndrome (XXY), fragile X syndrome, Turner syndrome, metafemales or trisomy X (XXX syndrome, 47,XXX aneuploidy), and monosomy X.

In addition, the enrichment methods can also be used to detect locus- and allele-specific sequences of interest, for example, autosomal and sex chromosomal point mutations, deletions, insertions, and translocations, which can be associated disease. Examples of translocations associated with disease include, for example, t(9;22)(q34;q11)—Philadelphia chromosome, CML, ALL; t(2;5)(p23;q35) (anaplastic large cell lymphoma); t(8;14)—Burkitt's lymphoma (c-myc); t(8;21)(q22;q22)—acute myeloblastic leukemia with maturation (AML1-ETO); t(12;21)(p12;q22)—ALL (TEL-AML1); t(12;15)(p13;q25)—(TEL-TrkC); t(9;12)(p24;p13)—CML, ALL (TEL-JAK2); acute myeloid leukemia, congenital fibrosarcoma, secretory breast carcinoma; t(11;14)—Mantle cell lymphoma (cyclin D1); t(11;22)(q24;q11.2-12)—Ewing's sarcoma; t(14;18)(q32;q21)—Follicular lymphoma (Bcl-2); t(15;17)—Acute promyelocytic leukemia; t(1;12)(q21;p13)—Acute myelogenous leukemia; t(17;22)—DFSP; and t(X;18)(p11.2;q11.2)—Synovial sarcoma.

Methods for determining fetal aneuploidy using random sequencing techniques are described, for example, in U.S. Patent Application Publication Nos. 20090029377 and 20090087847, Fan H C et al. (2008) *PNAS* 105:16266-71, and U.S. Provisional Patent Application Nos. 61/296,358 and 61/296,464, which are herein incorporated by reference in their entireties. The methods of fetal aneuploidy determination can be based on the fraction of fetal DNA in a sample. Such methods are described, for example, in U.S. Provisional Patent Application No. 61/296,358.

Aneuploidy can be suspected or determined when the number of enumerated sequences is greater than a predetermined amount. The predetermined amount can be based on estimated amount of DNA in a cell-free DNA sample. The predetermined amount can be based on the amount of enumerated sequences from a control region.

Library Formation

In another aspect, a method is provided for generating a library of selectively enriched non-random polynucleotide sequences comprising a) amplifying one or more polynucleotide sequences with a first set of oligonucleotide pairs, b) amplifying the product of a) with a second set of oligonucleotides pairs; and c) amplifying the product of b) with a third set of oligonucleotide pairs.

The polynucleotide sequences can be those enriched by the methods of the provided invention. The first set of oligonucleotide pairs can comprise sequence that distinguishes polynucleotides in one sample from polynucleotides in another sample. The first set of oligonucleotide pairs can comprise sequence that distinguishes polynucleotides in one sample from polynucleotides in another sample and sequence that extends the length of the product. Bridge amplification in Illumina (SOLEXA) sequencing can be most effective when the sequences are 100-500 bp. Fetal nucleic acid sequences are often less than 250 bp, and sequences of less than 100 bp can be amplified from cell-free samples. Thus, the sequence that extends the length of the product can facilitate SOLEXA sequencing. The polynucleotide sequences can be sequences enriched using the methods described herein.

In another aspect, a method for labeling enriched polynucleotides in two or more samples that allows identification of which sample the polynucleotide originated is provided, comprising: a) amplifying one or more polynucleotide sequences in two or more samples with a first set of oligonucleotide pairs, wherein the first set of oligonucleotide pairs comprises sequence that distinguishes polynucleotides from one sample from polynucleotides in another sample, b) amplifying the product of a) with a second set of oligonucleotides pairs; and c) amplifying the product of b) with a third set of oligonucleotide pairs.

In another aspect, a kit is provided comprising a) a first set of oligonucleotide primer pairs comprising: sequence that selectively hybridizes to a first set of genomic DNA sequences and sequence in-common amongst each of the first set of oligonucleotide primer pairs, b) a second set of oligonucleotide primer pairs with sequence that selectively hybridizes to the common sequence of the first set of oligonucleotide primer pairs and sequence common to the second set of oligonucleotide pairs, and c) a third set of oligonucleotide primer pairs with sequence that selectively hybridizes to the common sequence of the second set of oligonucleotide pairs.

The first set of primers can comprise sequence that distinguishes polynucleotides in one sample from polynucleotides in another sample.

The common region in the first set of primers can comprise sequence that distinguishes polynucleotides in one sample from polynucleotides in another sample and that extends the length of the product.

In another aspect, a kit is provided comprising: a first set of primer pairs that selectively amplifies a set of genomic sequences to create a first set of amplification products, a second set of primer pair that selectively amplifies the first set of amplification products, and a third set of primer pairs that selectively amplifies the second set of amplification products.

EXAMPLES

Example 1

"Hot Spot" Amplification Strategy

FIG. 1 illustrates a strategy for selecting sequences from chromosome 21 for enrichment. In step 100, sequence run data was combined. Total chromosome 21 sequence reads were used (102). These samples can include reads from samples that contain trisomy 21. "Hot" and "cold" regions of sequence coverage were mapped on chromosome 21 (104). For example, the region examined can be within a 5.8 Mb Down syndrome critical region (DSCR). PCR primers are designed, which can anneal to intergenic DNA or intragenic DNA (106). The primers were designed to anneal specifically with chromosome 21. The regions to be amplified can be a hot spot region, or region to which a number of sequence reads map (108). The PCR fragments generated can be approximately 200 bp in length. Next, sequencing analysis is performed using BioAnalyzer analysis and/or PCR/probe analysis (110).

Figure 2:
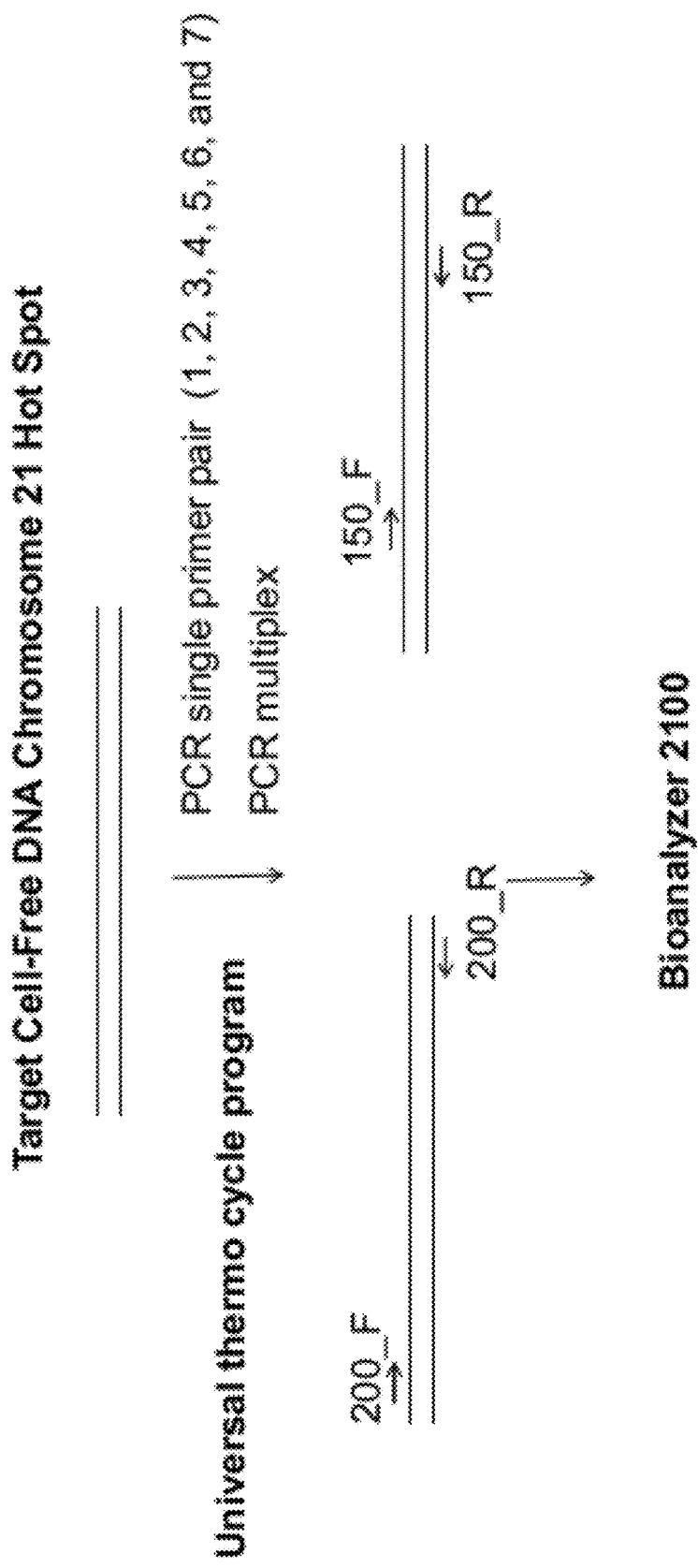
FIG. 2 illustrates a PCR scheme for "hot spot" enrichment.

PCR primers were designed to generate amplicons of approximately 200 bp and 150 bp from cell-free DNA template, as depicted is shown in FIG. 2. PCR amplification was performed using both simplex and multiplex reactions. The size of the amplicons was analyzed by Agilent 2100 Bioanalyzer and DNA 1000 kit. Sequences for primer pairs 1_150, 2_150, 3_150, 4_150, 5_150, 6_150, and 7_150 regions amplification, used in generating the data in FIGS. 2, 3, 4, and 5, are shown in Table 1.

Figure 4:
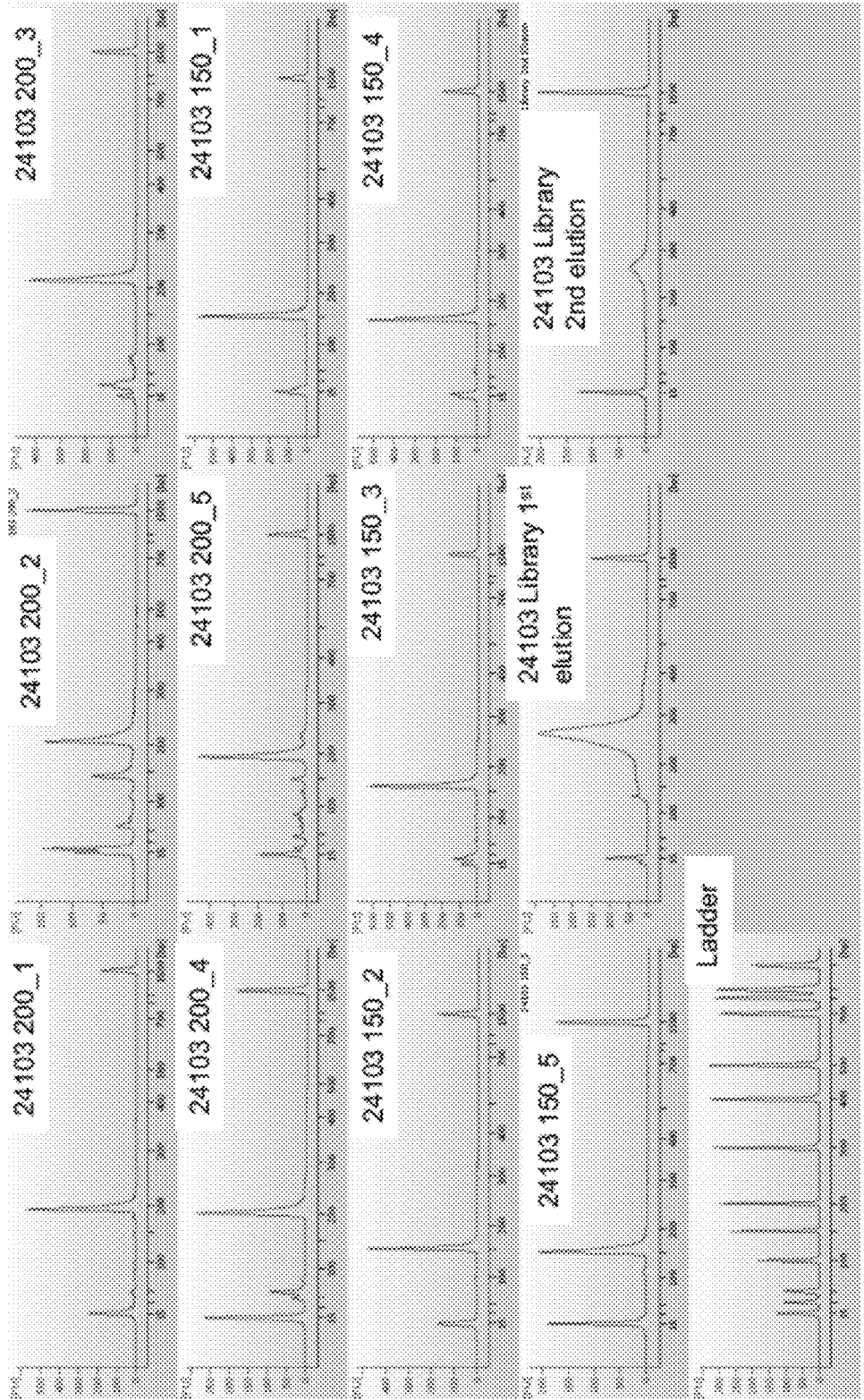
FIG. 4 illustrates simplex PCR amplification Bioanalyzer results.
Figure 6:
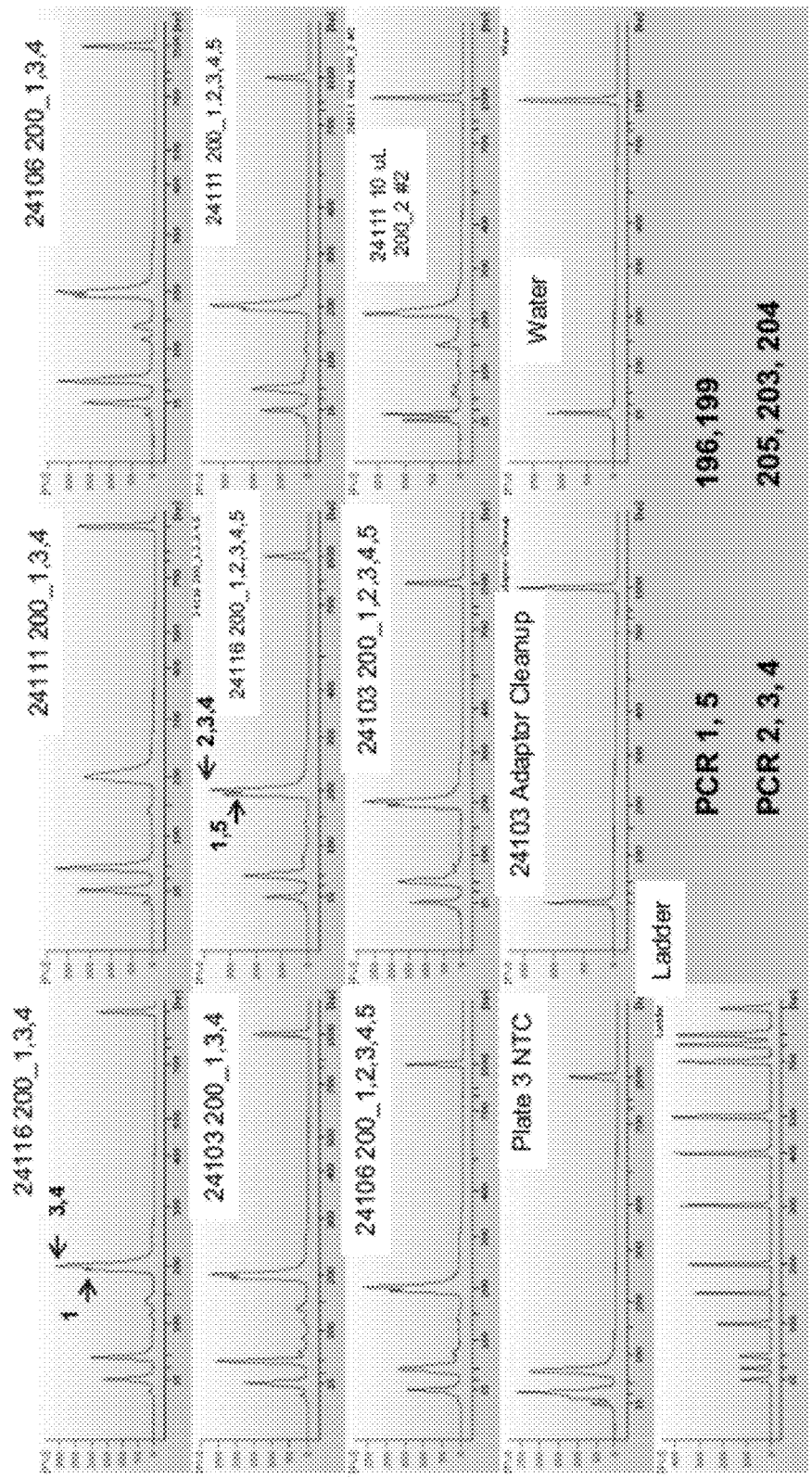
FIG. 6 illustrates multiplex PCR amplification Bioanalyzer results.

Primer sequences for 1_200, 2_200, 3_200, 4_200, 5_200, and 6_200 regions amplification, for FIGS. 2, 4, and 6, are illustrated in Table 2.

TABLE 1

Sequences for primer pairs 1_150, 2_150, 3_150, 4_150, 5_150, 6_150, and 7_150 (SEQ ID NOS: 1-14, respectively, in order of appearance).

| Chromosome Location | Primer Name | Primer Sequence | PCR Size (bp) |
|---|---|---|---|
| (1) Chr21: 45, 651, 908-45, 652, 158 | 1_150_45652158_F | CCCCAAGAGGTGCTTGTAGT | 155 |
| | 1_150_45652158_R | GCCATGGTGGAGTGTAGGAG | |
| (2) Chr21: 46, 153, 568-46, 153, 825 | 2_150_46153825_F | CTGAAGTGCTGCCAACACAC | 153 |
| | 2_150_46153825_R | TGATCTTGGAGCCTCCTTTG | |
| (3) Ch21: 46, 048, 091-46, 048, 339 | 3_150_46, 048, 339_F | AGCTTCTCCAGGACCCAGAT | 151 |
| | 3_150_46, 048, 339_R | CATTCATGGGAAGGGACTCA | |
| 4) Chr21: 46, 013, 033-46, 013, 258 | 4_150_46, 013, 258_F | CCATTGCACTGGTGTGCTT | 155 |
| | 4_150_46, 013, 258_R | GAGACGAGGGGACGATAGC | |
| (5) Chr21: 40,372, 444-40, 372, 655 | 5_150_40, 372, 655_F | TGCCATCGTAGTTCAGCGTA | 152 |
| | 5_150_40, 372, 655_R | TTGGACCACAGCTCAGAGG | |
| (6) Chr21: 41, 470, 712-41, 470, 747 | 6_41, 470, 712-150_F | AAAGTGTGCTTGCTCCAAGG | 152 |
| | 6_41, 470, 712-150_R | GGCAAAACACAGCCCAATAG | |
| (7) Chr21 | Ch21_APP150_F | CCTAGTGCGGGAAAAGACAC | 145 |
| | Ch21_APP150_R | TTCTCTCCCTTGCTCATTGC | |

TABLE 2

Sequences for primer pairs 1_200, 2_200, 3_200, 4_200, 5_200, and 6_200 (SEQ ID NOS: 15-26, respectively, in order of appearance).

| Chromosome Location | Primer Name | Primer Sequence | PCR Size (bp) |
|---|---|---|---|
| (1) Chr21: 45, 651, 908-45, 652, 158 | 1_45651908-45652158_F | GAGTCAGAGTGGAGCTGAGGA | 199 |
| | 1_45651908-45652158_R | GGAGGTCCTAGTGGTGAGCA | |
| (2) Chr21: 46, 153, 568-46, 153, 825 | 2_46153568-46153825_F | TGTGGGAAGTCAGGACACAC | 205 |
| | 2_46153568-46153825_R | GATCTTGGAGCCTCCTTTGC | |
| (3) Chr21: 46, 048, 091-46, 048, 339 | 3_46, 048, 091-46, 048, 339_F | GTGACAGCCTGGAACATGG | 203 |
| | 3_46, 048, 091-46, 048, 339_R | CAAGGCACCTGCACTAAGGT | |
| (4) Chr21: 46, 013, 033-46, 013, 258 | 4_46, 013, 033-46, 013, 258_F | TGCCTCCTGCTACTTTTACCC | 204 |
| | 4_46, 013, 033-46, 013, 258_R | AGACGGAACAGGCAGAGGT | |
| (5) Chr21: 40, 372, 444-40, 372, 655 | 5_40372444-40372655_F | CAAGACACAAGCAGGAGAGC | 196 |
| | 5_40372444-40372655_R | CAGTTTGGACCACAGCTCAG | |

TABLE 2-continued

Sequences for primer pairs 1_200, 2_200, 3_200, 4_200, 5_200, and 6_200
(SEQ ID NOS: 15-26, respectively, in order of appearance).

| Chromosome Location | Primer Name | Primer Sequence | PCR Size (bp) |
|---|---|---|---|
| (6) Chr21: 41, 470, 710-41, 471, 028 | 6_41470710_200F | AAAGTGTGCTTGCTCCAAGG | 194 |
| | 6_41470710-200R | TGGAACAAGCCTCCATTTTC | |

TABLE 3

Figure 7:
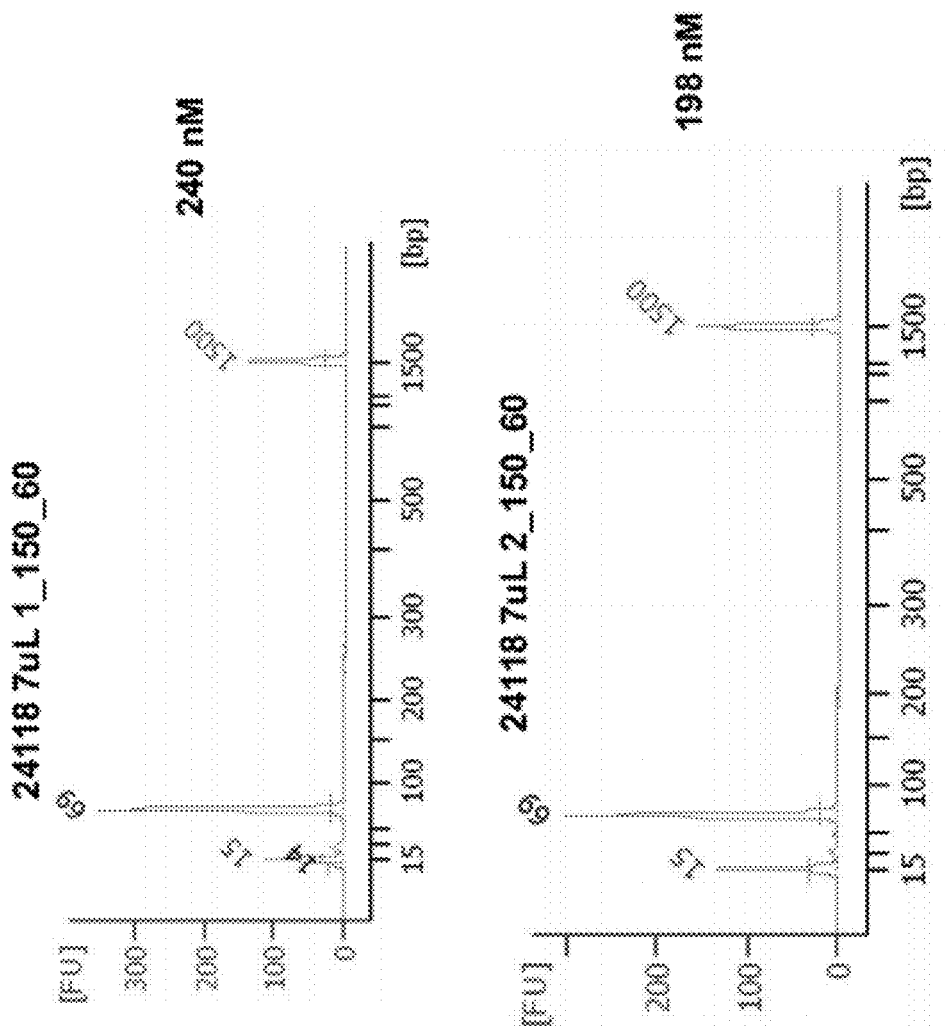
FIG. 7 illustrates PCR amplification of approximately 60 bp amplicons from chromosome 21.
Figure 8:
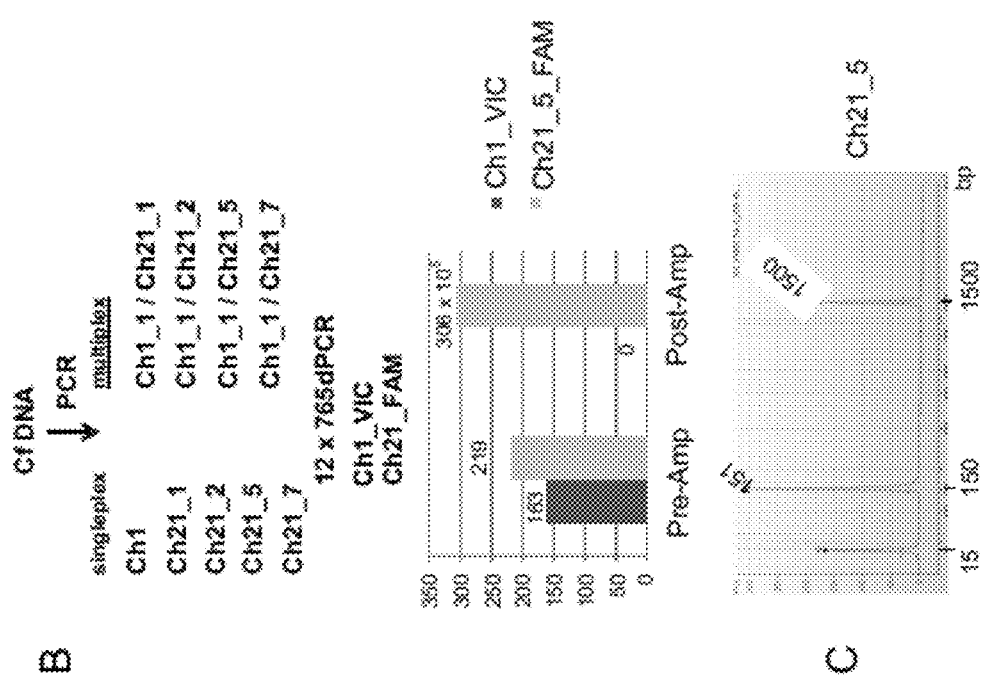
FIG. 8 illustrates Fluidigm digital PCR analysis evidence of chromosome 21 and 1 amplification.

Primer sequences for 1_150_60 and 2_150_60 region PCR amplification (FIG. 7);
same primer plus probe sequences for FIG. 8 (SEQ ID NOS: 27-41, respectively,
in order of appearance).

| Chromosome Location | Primer Name | Primer Sequence | PCR Size (bp) |
|---|---|---|---|
| (1) Chr21: 45, 651, 908-45, 652, 158 | 1_150_60_45652158_F | GAGGTGCTTGTAGTCAGTGCTTCA | 64 |
| | 1_150_60_45652158_R | CCCGGTGACACAGTCCTCTT | |
| | 1_150_60_45652158_P | AGTCAGAGTGGAGCTGAG | |
| (2) Chr21: 46, 153, 568-460, 153, 825 | 2_60_150_46153825_F | TGCTGCCAACACACGTGTCT | 60 |
| | 2_60_150_46153825_R | CAGGGCTGTTGCTCATGGA | |
| | 2_60_150_46153825_P | TCCCCTAGGATATCATC | |
| (5) Chr21: 40, 372, 444-40, 372, 655 | 5_60_150_40372655_F | CCCGCATCTGCAGCTCAT | 65 |
| | 5_60_150_40372655_R | TCTCTCCAAGTCCTACATCCTGTATG | |
| | 5_60_150_40372655_P | CCAGGTGGCTTCC | |
| Ch21 | 7_Amyloid_21_F | GGG AGC TGG TAC AGA AAT GAC TTC | ref. 1 |
| | 7_Amyloid_21_R | TTG CTC ATT GCG CTG ACA A | |
| | 7_Amyloid_21_P | AGC CAT CCT TCC CGG GCC TAG G | |
| Ch1 | ch1_1_F | GTTCGGCTTTCACCAGTCT | ref. 1 |
| | ch1_1_R | CTCCATAGCTCTCCCCACT | |
| | ch1_1_P | CGCCCTGCCATGTGGAA | |

Ref. 1 in Table 3 refers to Fan H C et al. (2008) *PNAS* 105: 16266-16271, which is herein incorporated by reference in its entirety. FIG. 3 illustrates amounts of nucleic acids that were detected for different samples of cell-free plasma DNA using different primers. FIG. 4 illustrates simplex PCR Amplification Bioanalyzer results, some of which correspond to the data in FIG. 3.

FIG. 5 illustrates results of PCR amplification of chromosome 21 in singleplex reactions. FIG. 6 illustrates Bioanalyzer results for multiplex PCR amplifications of chromosome 21. FIG. 7 illustrates Bioanalyzer results for PCR amplifications of approximately 60 bp amplicons. Table 3 illustrates primer sequences for 1_150_60 and 2_150_60 region PCR amplification.

FIG. 8A illustrates enrichment of chromosome 1 and 21 sequence. Four different sequences from chromosome 21 were amplified, as well a region from chromosome 1. Numbers of molecules were counted by dPCR. The ratio of the different sequences of chromosome 21 to chromosome 1 sequences from samples that underwent enrichment was calculated. Also provided are the ratio of chromosome 21 to 1 sequences from non-enriched (cf plasma DNA) samples. Also, genomic DNA was extracted from a cultured T21 cell line (Down Syndrome in origin) as positive control to show that dPCR primer/probe can amplify the ch21. The T21 cell line was ordered from ATCC and cultured in the lab: ATCC number: CCL-54; Organism: Homo sapiens; Morphology: fibroblast; Disease: Down syndrome; Gender: male; Ethnicity: Caucasian.

FIG. 8B illustrates a comparison of chromosome 1 and 21 counts pre-amplification (left side). Shown on the right side of the chart is the state following enrichment for ch21_5 using 5_60_150 primers (Table 3); amplified sequences were probed with chromosome 1-VIC and chromosome 21-FAM probes (Table 3). Only Ch21_5 sequence was amplified. FIG. 8C illustrates the size of an enriched fragment, ch21_5, using 5_60_150 primers (Table 3).

Figure 9:
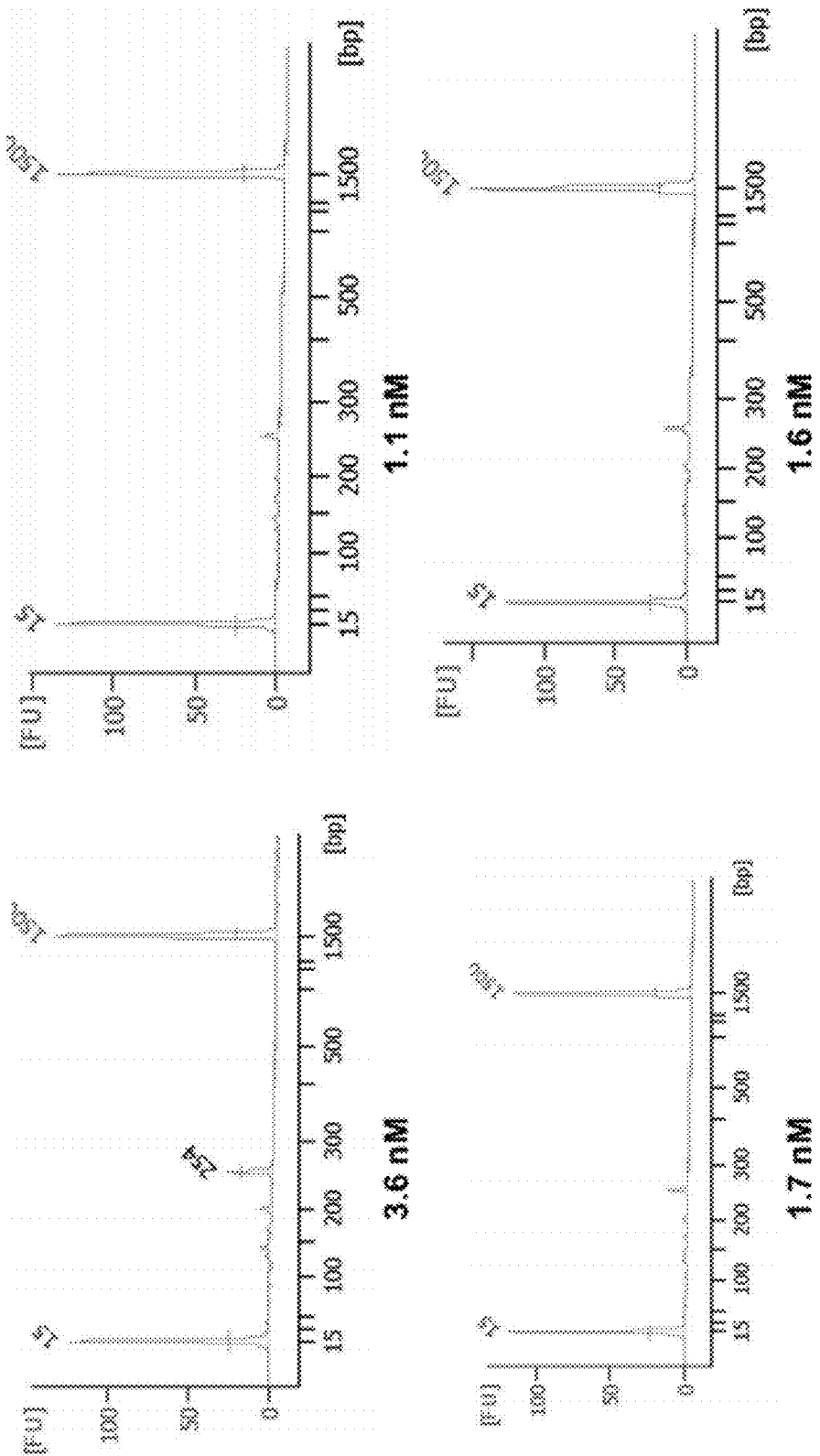
FIG. 9 illustrates size and concentration of DNA library construction conditions for PCR enrichment of chromosome 21 fragments in 4 different conditions.

A DNA library was generated with 24103_5_150 PCR fragment using Illumina ChIP-Seq Sample Preparation kit in 4 different conditions. The size and concentration of the generated DNA library was analyzed using Bioanalyzer shown in FIG. 9.

This DNA library was sequenced using an Illumina GA Sequencer and the sequences was analyzed with Illumina Pipeline software. The output sequencing reads were aligned to a human reference sequence. The correct and unique aligned sequences were then scored, of which 20% and 12% are exactly the same sequences of forward and reverse primer sequences and adjacent flanking sequences, respectively, as shown in the FIG. 10.

Example 2

Chromosome Walk Strategy for Sequence Enrichment

Figure 11:
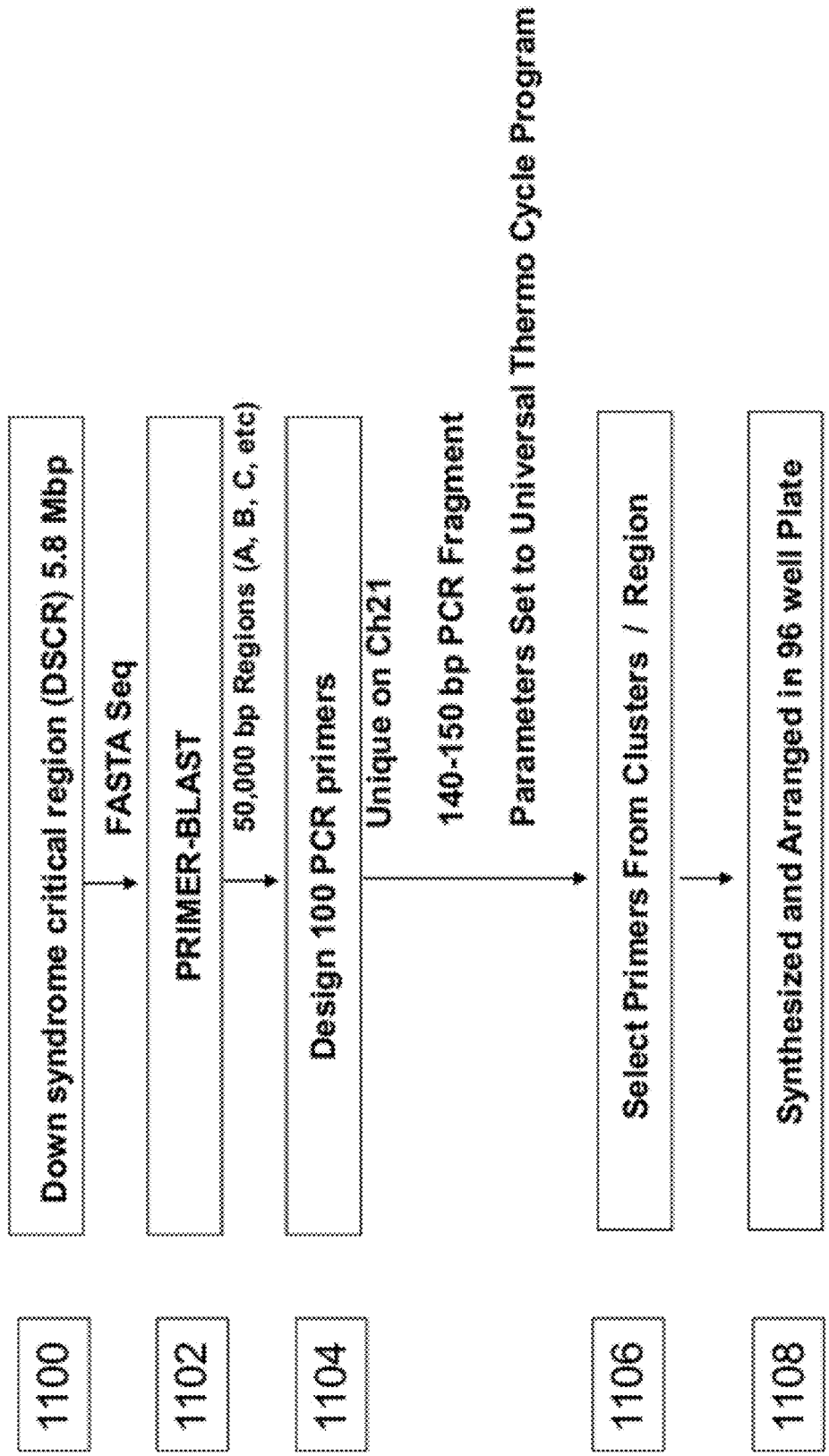
FIG. 11 illustrates strategy for design of PCR primers for the "chromosome walk" method of amplification.

FIG. 11 illustrates an overview of the chromosome walk strategy for sequence enrichment. A 5.8 Mbp Down syndrome critical region was selected (1100). PRIMER-BLAST (1102) was used to design 100 PCR primers (1104) in 50,000 bp regions. Unique sequences on chromosome 21 were sought to generate approximately 140-150 bp fragments. Primers were selected from different clusters in different regions on chromosome 21 (1106) and synthesized and arranged in 96 well plates (1108).

Figure 13:
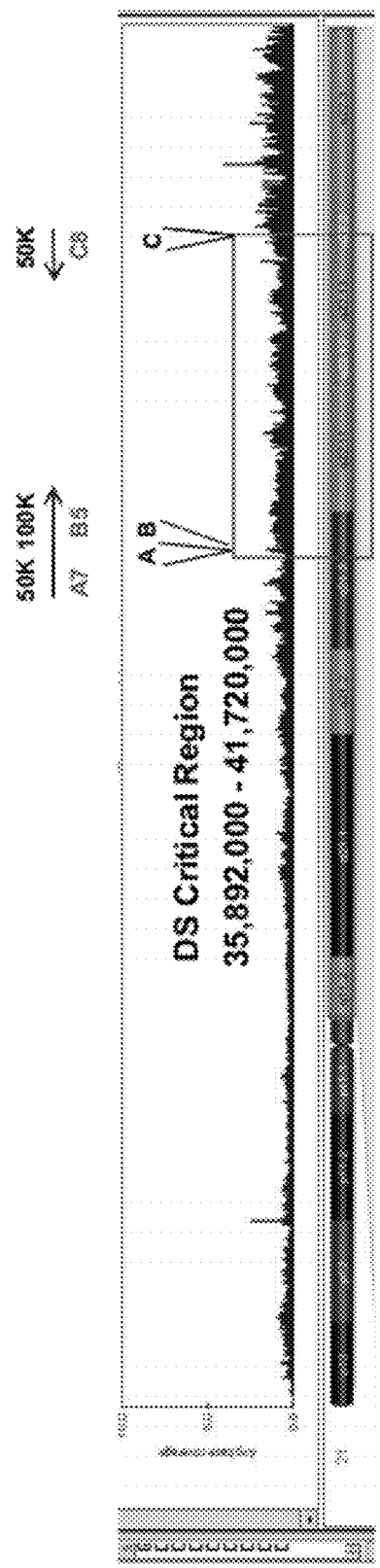
FIG. 13 illustrates relative position of regions A, B, C, and a Down syndrome critical region on a schematic of chromosome 21.
Figure 14:
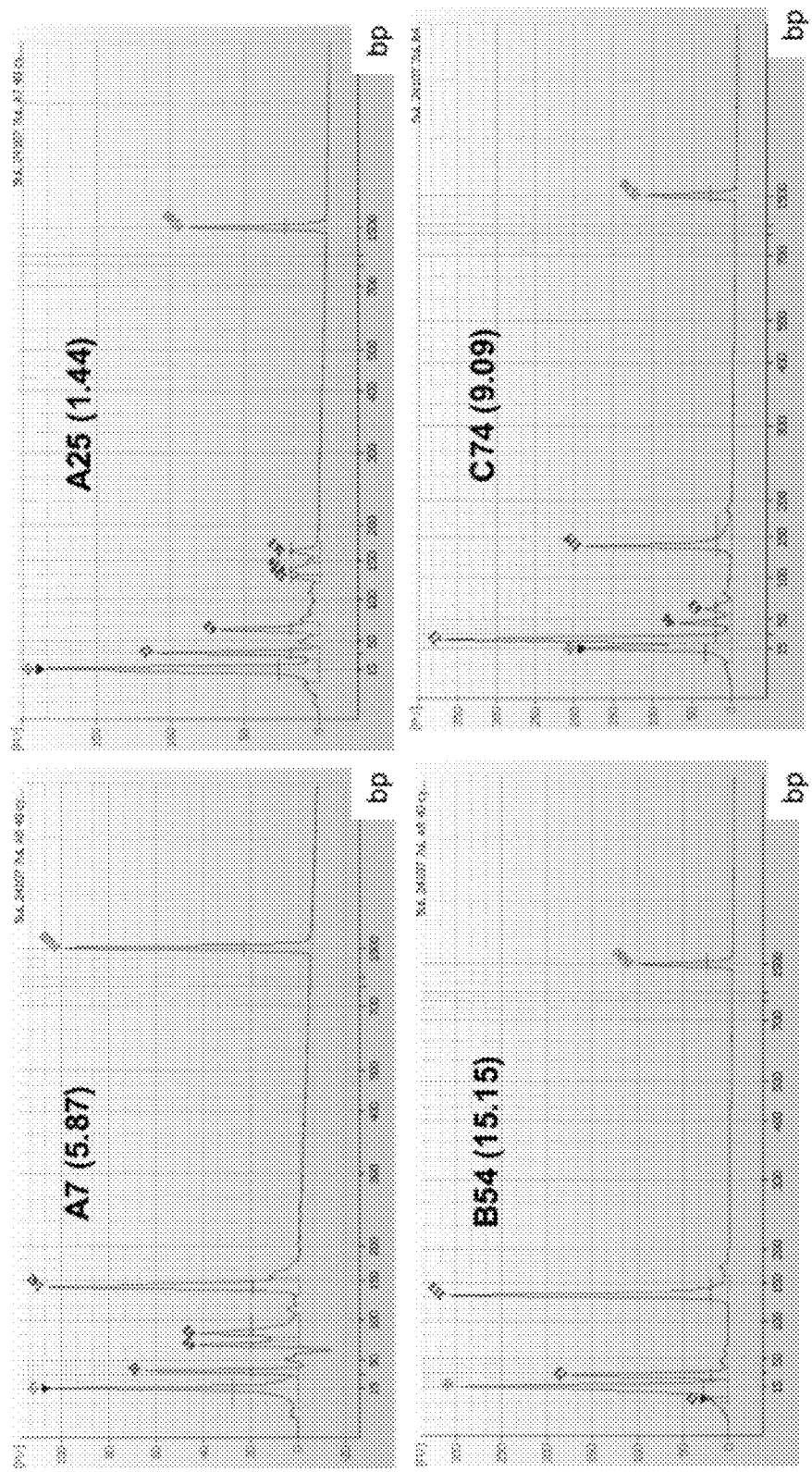
FIG. 14 illustrates PCR amplification results using the "chromosome walk" method of sequence selection.

FIG. 12 illustrates a primer pair that was designed, indicating length, annealing position on chromosome 21, melting temperature ($T_m$), and percent GC content. FIG. 13 illustrates the positions of three 50 kbp regions in a Down syndrome critical region on chromosome 21. FIG. 14 illustrates Bioanalyzer results of PCR amplification of different sequences from clusters A, B, and C in regions A, B, and C on chromosome 21. FIG. 15 illustrates amplification results from different clusters in regions A, B, and C of chromosome 21, one primer pair/cluster.

Figure 16:
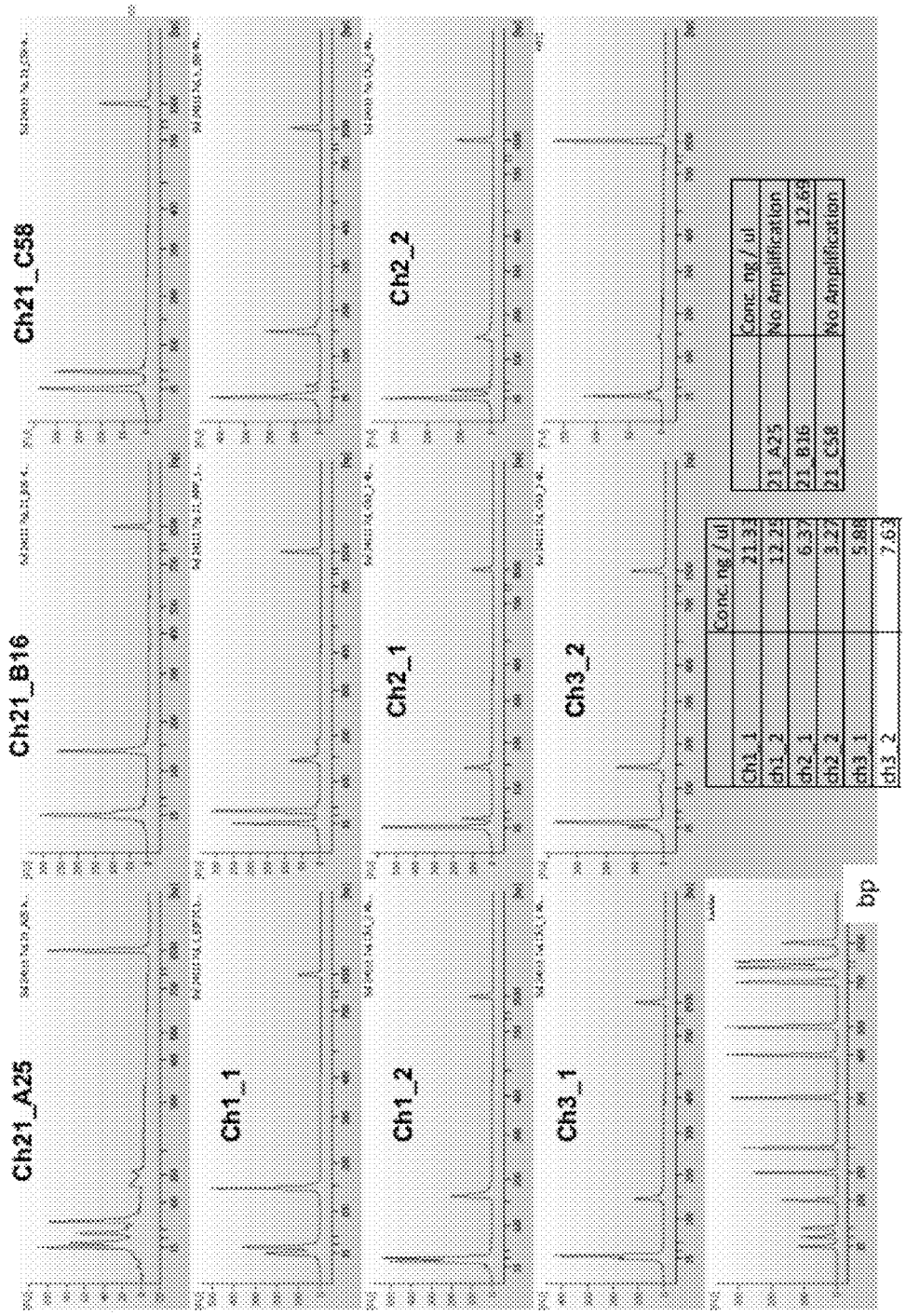
FIG. 16 illustrates enrichment of chromosome 21 sequence and reference chromosome 1, 2, and 3 sequences.

FIG. 16 illustrates PCR amplification of chromosome 21 and reference chromosome 1 sequences. Ch21_A25, ch21_B16, and ch21_C58 are sequences selected using chromosome walk strategy. Ch1_1, ch1_2, ch2_1, ch2_2, ch3_1, ch3_2 are sequences selected using "hot spot" strategy. The sequences of primers used to generate data in FIGS. 15 and 16 are in Table 4.

TABLE 4

Primer sequences used to generate data in FIGS. 15, 16, and 17 (SEQ ID NOS: 42-95, respectively, in order of appearance).

| | | |
|---|---|---|
| A18_F_22632000 | TGAAGCCCGGGAGGTTCCCT | |
| A18_R_22632000 | TCCAGGCTGTGTGCCCTCCC | |
| A2_F_22632000 | GCCAGGCTGCAGGAAGGAGG | |
| A2_R_22632000 | GTTAGGGGAGGGCACGCAGC | |
| A28_F_22632000 | CCAGCACCACACACCAGCCC | |
| A28_R_22632000 | GCAGAAAGCTCAGCCTGGCCC | |
| A72_F_22632000 | TCCAGTCCTGCACCCTCTCCC | |
| A72_R_22632000 | GGTGGCTCGGGGCTCCTCAT | |
| A7_F_22632000 | CAGTGTCCCCACGCACTCACG | |
| A7_R_22632000 | TCCAGCACCTCCAGCCTCCC | |
| A73_F_22632000 | CTGTGGTCAGCAGTCGCACGC | |
| A73_R_22632000 | TCCCCTTGGCCTGCCATCGT | |
| A25_F_22632000 | GGACCATGGCAACGGCCTCC | |
| A25_R_22632000 | TCCAACAGGCGGTGTCAAGCC | |
| B16_F_22681999 | GCCAAGCCTGCCTTGTGGGA | |
| B16_R_22681999 | GGTGCCCTCCCTCACGATGC | |
| B19_F_22681999 | GTGGGCACTTCAGAGCTGGGC | |
| B19_R_22681999 | GTGGGATGTGCCCTCGTGCC | |
| B54_F_22681999 | CCCGCCTTGTTGGGTACGAGC | |
| B54_R_22681999 | GAGCGGGGAGCAGGATGGGT | |
| B34_F_22681999 | TCCCAGAATGCCACGCCCTG | |
| B34_R_22681999 | GAGGTGTGTGCTGAGGGGCG | |
| B32_F_22681999 | ACTCTGTCCCGTGCCCTTGCT | |
| B32_R_22681999 | CAAGGCGCCCTTGACTGGCA | |
| B7_F_22681999 | ATGCCATGCCCAACGCCACT | |
| B7_R_22681999 | CTGTGGCCTCAGCTGCTCGG | |
| C1_F_28410001 | CTGTGGGCCGCTCTCCCTCT | |
| C1_R_28410001 | CCTCCGGTAGGGCCAAGGCT | |
| C58_F_28410001 | TGACCTGTGGGCCGCTCTCC | |
| C58_R_28410001 | CCTCCGGTAGGGCCAAGGCT | |
| C6_F_28410001 | CAGCCCTGTGAGGCATGGGC | |
| C6_R_28410001 | AGTGAGAGGAGCGGCTGCCA | |
| C74_F_28410001 | GGGGCTGGTGGAGCTGGTGA | |
| C74_R_28410001 | TGGAGCCCCACATCCTGCGT | |
| C19_F_28410001 | TGTTCCCCGTGCCTGGCTCT | |
| C19_R_28410001 | TGGGGCCCATCCTGGGGTTC | |
| C29_F_28410001 | TGATGGCACGTGTTGCCCCG | |
| C29_R_28410001 | ACCGTGGCTGACCCCTCCTC | |
| C72_F_28410001 | CGCCGGGACACAGGAAGCAC | |
| C72_R_28410001 | CCCTGGTGAGGAGCCGGGAG | |
| C55_F_28410001 | GCCAGGGAAGGACTGCGGTG | |
| C55_R_28410001 | CAGCCAGGGCAGGACTCGGA | |
| Ch1_1_150_F | GAGGTCTGGTTCGGCTTTC | ref. 1 |
| Ch1_1_150_R | CAGAGCTGGGAGGGATGAG | ref. 1 |
| ch1_2_150_F | TGCAACAGCTTCGTTGGTAG | |
| ch1_2_150_R | TAGGTCCAGCAGGAAGTTGG | |
| ch2_1_150_F | GTCGGAGAAGATCCGTGAGA | |
| ch2_1_150_R | CCAGGCATCAATGTCATCAG | |
| ch2_2_150_F | TGTCAACCAGACGTTCCAAA | |
| ch2_2_150_R | TAACACAGCTGGTGCCTGAG | |
| ch3_1_150_F | ATTCCCCCTTAACCACTTGC | |
| ch3_1_150_R | GAGGGTGTCTCGCTTGGTC | |
| ch3_2_150_F | GCTGAGTAGGAAATGGGAGGT | |
| ch3_2_150_R | CTGCAGTCAGGGAGCAGAGT | |

FIG. 17 illustrates PCR amplification of reference chromosomes 1, 2, and 3. Primer sequences used to generate data are shown in Table 4.

FIG. 18 illustrates a comparison of amplification success rate using the "chromosome walk" method and the "hot spot" sequence selection method. 76% (16/21) amplifications of chromosome 21 were successful using the "chromosome walk" method to select sequences. 100% (7/7) sequences selected based on "hot spots" on chromosome 21 amplified.

100% (5/5) sequences selected based on "hot spots" on chromosomes 1, 2, and/or 3 amplified.

Example 3

Selection of Hotspot Region for Amplification

Figure 19:
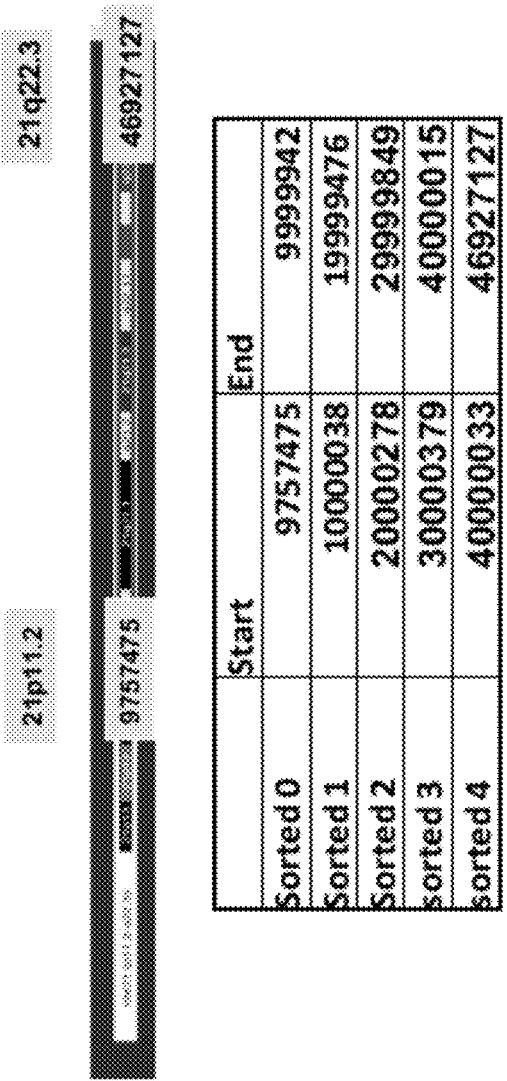
FIG. 19 illustrates sequence coverage of chromosome 21.
Figure 20:
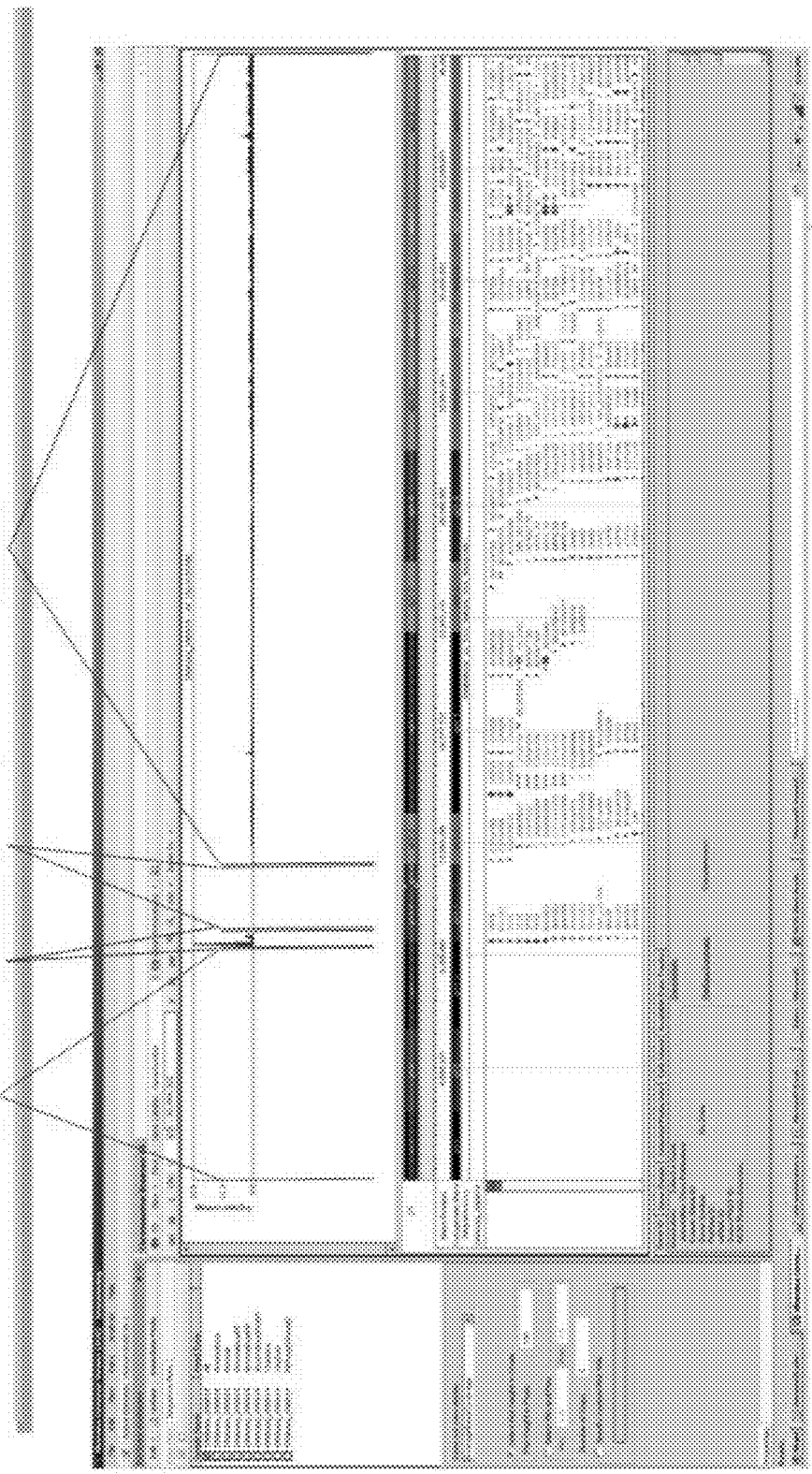
FIG. 20 highlights different regions of sequence coverage mapped to a schematic of chromosome 21.
Figure 25:
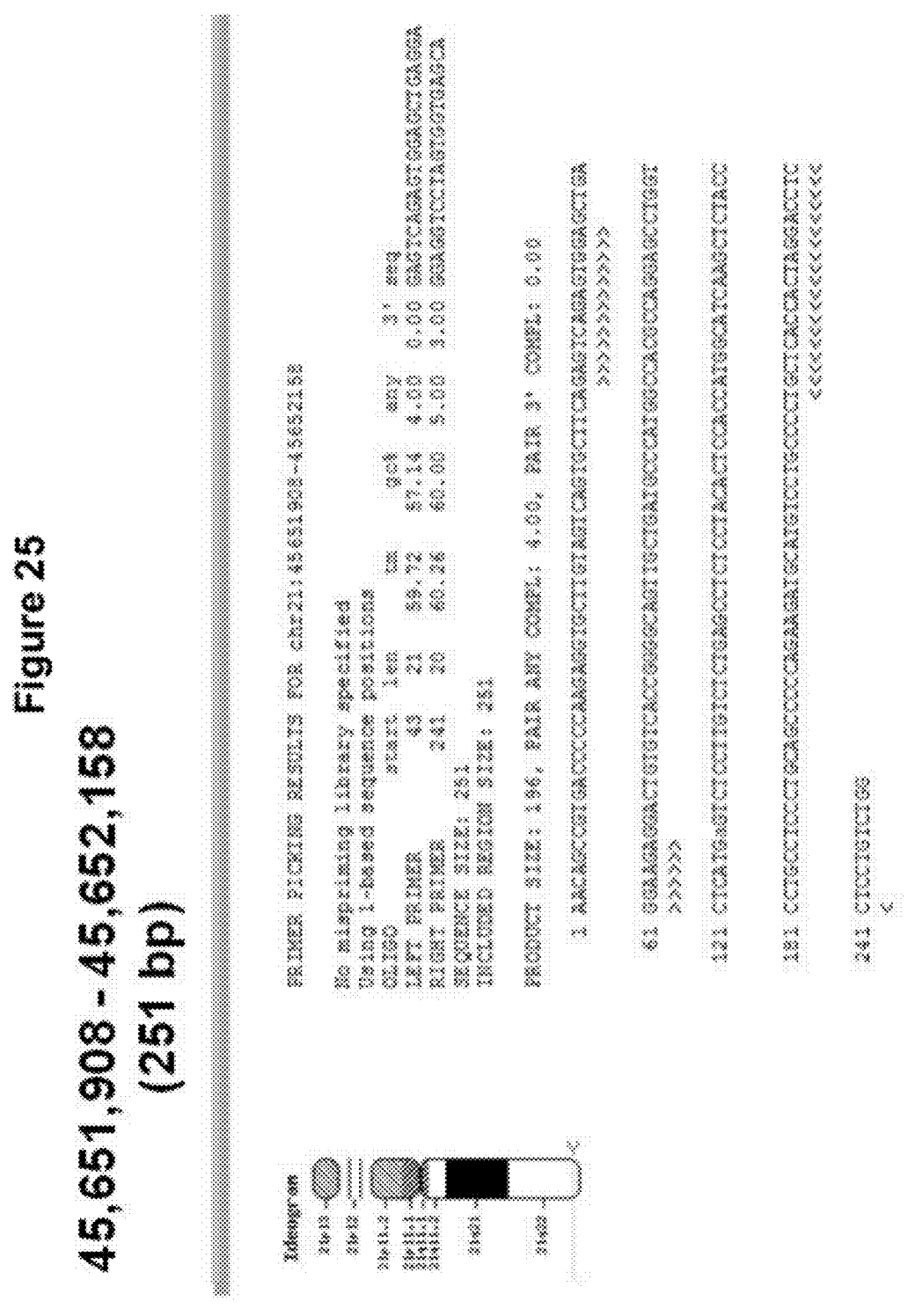

Sequences for enrichment can be chosen on the basis of being in a "hotspot," a region of relatively high sequence coverage. FIG. 19 illustrates that sequence runs from multiple samples were combined to give 79% coverage of chromosome 21. The bottom chart illustrates Illumina pipeline output files containing multiple files and each given start and end chromosome positions; therefore the sequencing reads cover 37 M region (46,927,127 last position–9,757,475 1st position=~37 M). FIG. 20 shows a schematic of chromosome 21 to which sequence reads have been mapped. Some regions have more sequence coverage than other regions. FIG. 21 illustrates an example of a process that was used to select a specific region of 251 base pairs for amplification. Sequence within 13,296,000-46,944,323 (illustrated in FIG. 20) was selected for amplification. FIGS. 22A and B illustrate the relative position for a Down syndrome critical region (35,892,000-41,720,000) on chromosome 21. Magnified views of the sequence reads mapped to chromosome 21 are shown in FIG. 23. FIG. 24 illustrates sequence reads that map to a 4207 bp region on chromosome 21 and a 251 bp region within that 4207 bp region. The Y axis is the number of sequence reads at a chromosome position. FIG. 25 illustrates a primer pair that was designed to anneal to sequence with the 251 bp region.

Example 4

Nested PCR for DNA Library Construction

Figure 26:
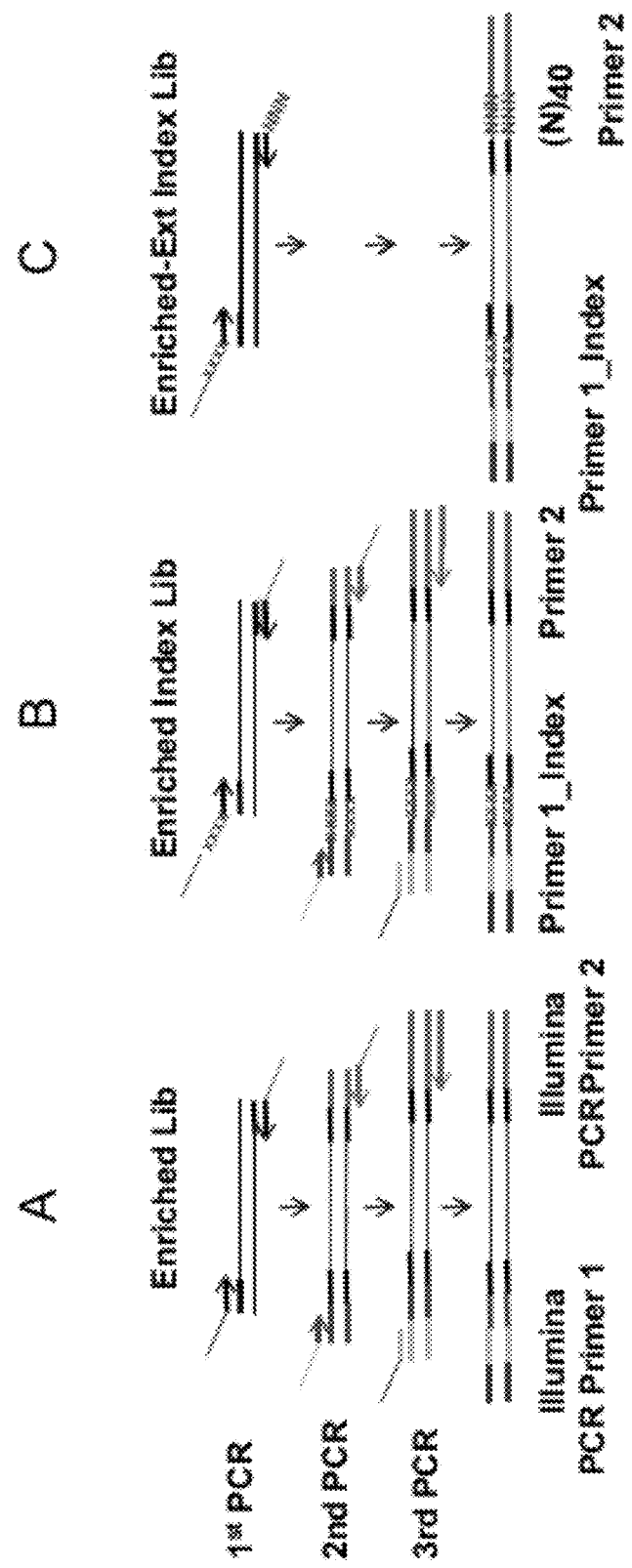
FIG. 26 illustrates a nested PCR strategy for DNA library construction.

FIG. 26 illustrates methods for generating library of enriched sequences. In the scheme shown in FIG. 26A, a three step PCR amplification process is used to generate a library of enriched nucleic acids where the fragments have sequence incorporated that can be used for annealing to primers for subsequent sequencing. A first pair of primers is used to amplify enriched sequences. These primers have sequence that anneals to a second set of primers that is used to amplify products of the first reaction. The second set of primers can have sequence that can anneal to sequencing primers. A third set of primers anneals to sequence from the first set of primers and is used further amplify the products. The third set of primers also introduces sequence onto the fragments that can anneal to sequencing primers.

The PCR scheme in FIG. 26B illustrates a means for indexing sequences. The enriched fragments from each sample (e.g., individual maternal cell-free samples) can have sequence incorporated that identifies the fragment as originating from that sample. This indexing allows multiple samples to be pooled without loss of information with respect to which sample a fragment originated. The three step PCR proceeds as shown in FIG. 26A with indexing sequence being incorporated in primers used in the first amplification step. The indexing sequence can be in primers used for the $1^{st}$, $2^{nd}$, or $3^{rd}$ amplification step.

The PCR scheme in FIG. 26C differs in that sequence is incorporated that serves to extend the length of enriched fragments. Fetal DNA in maternal cell-free samples is often less than 200 bp in size. Some amplifications enrich fragments that are, e.g., 60 bp in size. However, sequence reactions using, e.g., Illumina sequencing technology are more efficient when fragments are at least 100 bp in length. Thus, the PCR indexing scheme can be modified, e.g., as shown in FIG. 26C, to amplify fragments with sequence in the $1^{st}$, $2^{nd}$, or $3^{rd}$ step that serves to lengthen the fragments in the library.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for determining a presence or absence of a fetal aneuploidy in a fetus for each of a plurality of maternal blood samples obtained from a plurality of different pregnant women, said maternal blood samples comprising fetal and maternal cell-free genomic DNA, said method comprising:
   (a) obtaining a fetal and maternal cell-free genomic DNA sample from each of the plurality of maternal blood samples;
   (b) selectively enriching a plurality of non-random polynucleotide sequences of each fetal and maternal cell-free genomic DNA sample of (a) to generate a library derived from each fetal and maternal cell-free genomic DNA sample of enriched and indexed fetal and maternal non-random polynucleotide sequences, wherein each library of enriched and indexed fetal and maternal non-random polynucleotide sequences includes an indexing nucleotide sequence which identifies a maternal blood sample of the plurality of maternal blood samples,
   wherein said plurality of non-random polynucleotide sequences comprises at least 100 different non-random polynucleotide sequences selected from a first chromosome tested for being aneuploid and at least 100 different non-random polynucleotide sequences selected from a reference chromosome, wherein the first chromosome tested for being aneuploid and the reference chromosome are different, and wherein each of said plurality of non-random polynucleotide sequences is from 10 to 1000 nucleotide bases in length,
   (c) pooling the libraries generated in (b) to produce a pool of enriched and indexed fetal and maternal non-random polynucleotide sequences;
   (d) performing massively parallel sequencing of the pool of enriched and indexed fetal and maternal non-random polynucleotide sequences of (c) to produce sequence reads corresponding to enriched and indexed fetal and maternal non-random polynucleotide sequences of each of the at least 100 different non-random polynucleotide sequences selected from the first chromosome tested for being aneuploid and sequence reads corresponding to enriched and indexed fetal and maternal non-random polynucleotide sequences of each of the at least 100 different non-random polynucleotide sequences selected from the reference chromosome;
   (e) based on the indexing nucleotide sequence, for each of the plurality of maternal blood samples, enumerating sequence reads corresponding to enriched and indexed fetal and maternal non-random polynucleotide sequences selected from the first chromosome tested for being aneuploid and sequence reads corresponding to enriched and indexed fetal and maternal non-random polynucleotide sequences selected from the reference chromosome; and
   (f) for each of the plurality of maternal blood samples, determining the presence or absence of a fetal aneuploidy comprising using a number of enumerated sequence reads corresponding to the first chromosome and a number of enumerated sequence reads corresponding to the reference chromosome of (e).

2. The method of claim 1, wherein for each of the plurality of maternal blood samples determining the presence or absence of a fetal aneuploidy comprises comparing the number of enumerated sequence reads corresponding to the first chromosome tested for being aneuploid with the number of enumerated sequence reads corresponding to the reference chromosome.

3. The method of claim 1, wherein said plurality of non-random polynucleotide sequences comprises at least 300 different non-random polynucleotide sequences selected from the first chromosome tested for being aneuploid and at least 300 different non-random polynucleotide sequences selected from the reference chromosome.

4. The method of claim 3, wherein said plurality of non-random polynucleotide sequences comprises at least 500 different non-random polynucleotide sequences selected from the first chromosome tested for being aneuploid and at least 500 different non-random polynucleotide sequences selected from the reference chromosome.

5. The method of claim 1, wherein each of said plurality of non-random polynucleotide sequences is from 10 to 500 nucleotide bases in length.

6. The method of claim 1, wherein each of said plurality of non-random polynucleotide sequences is from 50 to 150 nucleotide bases in length.

7. The method of claim 1, wherein said first chromosome tested for being aneuploid is selected from the group consisting of chromosome 13, chromosome 18, chromosome 21, chromosome X, and chromosome Y.

8. The method of claim 7, wherein said fetal aneuploidy comprises fetal aneuploidy of a chromosome selected from the group consisting of chromosome 13, chromosome 18, chromosome 21, chromosome X, and chromosome Y.

9. The method of claim 8, wherein said fetal aneuploidy is selected from the group consisting of trisomy 21, trisomy 18, trisomy 13, and monosomy X.

10. The method of claim 1, wherein said reference chromosome is selected from the group consisting of chromosome 1, chromosome 2, chromosome 3, chromosome 13, chromosome 18, and chromosome 21.

11. The method of claim 1, wherein said fetal aneuploidy comprises monosomy, trisomy, tetrasomy, or pentasomy of the first chromosome.

12. The method of claim 1, wherein said selectively enriching of (b) comprises performing polymerase chain reaction (PCR) amplification.

13. The method of claim 12, wherein for each fetal and maternal cell-free genomic DNA sample PCR amplification comprises hybridizing at least two oligonucleotides to each of the at least 100 different non-random polynucleotide sequences selected from the first chromosome tested for being aneuploid and each of the at least 100 different non-random polynucleotide sequences selected from the reference chromosome.

14. The method of claim 13, wherein said oligonucleotides do not hybridize to non-random polynucleotide sequences comprising one or more polymorphisms.

15. The method of claim 13, wherein each of said oligonucleotides has a substantially similar melting temperature.

16. The method of claim 1, wherein said massively parallel sequencing generates at least 30 nucleotide bases per sequence read.

17. The method of claim 1, wherein said fetal aneuploidy comprises partial monosomy or partial trisomy.

18. The method of claim 1, wherein said plurality of non-random polynucleotide sequences comprises no more than 1000 different non-random polynucleotide sequences selected from the first chromosome tested for being aneuploid and no more than 1000 different non-random polynucleotide sequences selected from the reference chromosome.

19. A method for determining a presence or absence of a fetal aneuploidy in a fetus for each of a plurality of maternal blood samples obtained from a plurality of different pregnant women, said maternal blood samples comprising fetal and maternal cell-free genomic DNA, said method comprising:
 (a) obtaining a fetal and maternal cell-free genomic DNA sample from each of the plurality of maternal blood samples;
 (b) selectively enriching a plurality of non-random polynucleotide sequences of each fetal and maternal cell-free genomic DNA sample of (a) to generate a library derived from each fetal and maternal cell-free genomic DNA sample of enriched and indexed fetal and maternal non-random polynucleotide sequences, wherein each library of enriched and indexed fetal and maternal non-random polynucleotide sequences includes an indexing nucleotide sequence which identifies a maternal blood sample of the plurality of maternal blood samples,
 wherein said plurality of non-random polynucleotide sequences comprises at least 100 different non-random polynucleotide sequences selected from at least one chromosome region tested for being aneuploid and at least 100 different non-random polynucleotide sequences selected from at least one chromosome control region, wherein the at least one chromosome region tested for being aneuploid and the at least one chromosome control region are different, and wherein each of said plurality of non-random polynucleotide sequences is from 10 to 1000 nucleotide bases in length;
 (c) pooling the libraries generated in (b) to produce a pool of enriched and indexed fetal and maternal non-random polynucleotide sequences;
 (d) performing massively parallel sequencing of the pool of enriched and indexed fetal and maternal non-random polynucleotide sequences of (c) to produce sequence reads corresponding to enriched and indexed fetal and maternal non-random polynucleotide sequences of each of the at least 100 different non-random polynucleotide sequences selected from the at least one chromosome region tested for being aneuploid and sequence reads corresponding to enriched and indexed fetal and maternal non-random polynucleotide sequences of each of the at least 100 different non-random polynucleotide sequences selected from the at least one chromosome control region;
 (e) based on the indexing nucleotide sequence, for each of the plurality of maternal blood samples, enumerating sequence reads corresponding to enriched and indexed fetal and maternal non-random polynucleotide sequences selected from the at least one chromosome region tested for being aneuploid and sequence reads corresponding to enriched and indexed fetal and maternal non-random polynucleotide sequences selected from the at least one chromosome control region; and
 (f) for each of the plurality of maternal blood samples, determining the presence or absence of a fetal aneuploidy comprising using a number of enumerated sequence reads corresponding to the at least one chromosome region tested for being aneuploid and a number of enumerated sequence reads corresponding to the at least one chromosome control region of (e).

20. The method of claim 19, wherein for each of the plurality of maternal blood samples determining the presence or absence of a fetal aneuploidy comprises comparing the number of enumerated sequence reads corresponding to the at least one chromosome region tested for being aneuploid with the number of enumerated sequence reads corresponding to the at least one chromosome control region.

21. The method of claim 19, wherein said plurality of non-random polynucleotide sequences comprises at least 300 different non-random polynucleotide sequences selected from the at least one chromosome region tested for being aneuploid and at least 300 different non-random polynucleotide sequences selected from the at least one chromosome control region.

22. The method of claim 19, wherein each of said plurality of non-random polynucleotide sequences is from 10 to 500 nucleotide bases in length.

23. The method of claim 19, wherein the at least one chromosome region tested for being aneuploid is selected from at least one chromosome selected from the group consisting of chromosome 13, chromosome 18, chromosome 21, chromosome X, and chromosome Y.

24. The method of claim 23, wherein said fetal aneuploidy comprises fetal aneuploidy of a chromosome selected from the group consisting of chromosome 13, chromosome 18, chromosome 21, chromosome X, and chromosome Y.

25. The method of claim 24, wherein said fetal aneuploidy is selected from the group consisting of trisomy 21, trisomy 18, trisomy 13, and monosomy X.

26. The method of claim 19, wherein the at least one chromosome control region is selected from at least one chromosome selected from the group consisting of chromosome 1, chromosome 2, chromosome 3, chromosome 13, chromosome 18, and chromosome 21.

27. The method of claim 19, wherein said fetal aneuploidy comprises monosomy, trisomy, tetrasomy, or pentasomy of at least one chromosome.

28. The method of claim 19, wherein said selectively enriching of (b) comprises performing polymerase chain reaction (PCR) amplification.

29. The method of claim 28, wherein for each fetal and maternal cell-free genomic DNA sample PCR amplification comprises hybridizing at least two oligonucleotides to each of the at least 100 different non-random polynucleotide sequences selected from the at least one chromosome region tested for being aneuploid and each of the 100 different non-random polynucleotide sequences selected from the at least one chromosome control region.

30. The method of claim 19, wherein said plurality of non-random polynucleotide sequences comprises no more than 1000 different non-random polynucleotide sequences selected from the at least one chromosome region tested for being aneuploid and no more than 1000 different non-random polynucleotide sequences selected from the at least one chromosome control region.

* * * * *

SEQUENCE LISTING

```
<160> NUMBER OF SEQ ID NOS: 133

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccccaagagg tgcttgtagt                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
```

-continued gccatggtgg agtgtaggag                                                      20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctgaagtgct gccaacacac                                                      20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgatcttgga gcctcctttg                                                      20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agcttctcca ggacccagat                                                      20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cattcatggg aagggactca                                                      20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccattgcact ggtgtgctt                                                       19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gagacgaggg gacgatagc                                                       19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgccatcgta gttcagcgta                                                    20

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttggaccaca gctcagagg                                                     19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaagtgtgct tgctccaagg                                                    20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggcaaaacac agcccaatag                                                    20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cctagtgcgg gaaaagacac                                                    20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ttctctccct tgctcattgc                                                    20

<210> SEQ ID NO 15

<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
gagtcagagt ggagctgagg a                                              21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
ggaggtccta gtggtgagca                                                20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
tgtgggaagt caggacacac                                                20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
gatcttggag cctcctttgc                                                20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
gtgacagcct ggaacatgg                                                 19

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
caaggcacct gcactaaggt                                                20

<210> SEQ ID NO 21
<211> LENGTH: 21
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 21
tgcctcctgc tacttttacc c                                              21

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agacggaaca ggcagaggt                                                 19

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
caagacacaa gcaggagagc                                                20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cagtttggac cacagctcag                                                20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aaagtgtgct tgctccaagg                                                20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tggaacaagc ctccattttc                                                20

<210> SEQ ID NO 27
<211> LENGTH: 24
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 27
gaggtgcttg tagtcagtgc ttca                                              24

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cccggtgaca cagtcctctt                                                   20

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
agtcagagtg gagctgag                                                     18

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgctgccaac acacgtgtct                                                   20

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cagggctgtt gctcatgga                                                    19

<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
tcccctagga tatcatc                                                      17

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer <210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cccgcatctg cagctcat                                                    18

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tctctccaag tcctacatcc tgtatg                                           26

<210> SEQ ID NO 35
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
ccaggtggct tcc                                                         13

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gggagctggt acagaaatga cttc                                             24

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ttgctcattg cgctgacaa                                                   19

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
agccatcctt cccgggccta gg                                               22

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

-continued gttcggcttt caccagtct         19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ctccatagct ctccccact         19

<210> SEQ ID NO 41
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
cgccctgcca tgtggaa         17

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tgaagcccgg gaggttccct         20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tccaggctgt gtgccctccc         20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gccaggctgc aggaaggagg         20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gttaggggag ggcacgcagc         20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ccagcaccac acaccagccc                                                   20

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gcagaaagct cagcctggcc c                                                 21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tccagtcctg caccctctcc c                                                 21

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ggtggctcgg ggctcctcat                                                   20

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cagtgtcccc acgcactcac g                                                 21

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tccagcacct ccagcctccc                                                   20

```
<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ctgtggtcag cagtcgcacg c                                             21

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tccccttggc ctgccatcgt                                               20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ggaccatggc aacggcctcc                                               20

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tccaacaggc ggtgtcaagc c                                             21

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gccaagcctg ccttgtggga                                               20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ggtgccctcc ctcacgatgc                                               20

<210> SEQ ID NO 58
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gtgggcactt cagagctggg c                                          21

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gtgggatgtg ccctcgtgcc                                            20

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
cccgccttgt tgggtacgag c                                          21

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gagcggggag caggatgggt                                            20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tcccagaatg ccacgccctg                                            20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gaggtgtgtg ctgaggggcg                                            20

<210> SEQ ID NO 64
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 64
actctgtccc gtgcccttgc t                                              21

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
caaggcgccc ttgactggca                                                20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
atgccatgcc caacgccact                                                20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ctgtggcctc agctgctcgg                                                20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ctgtgggccg ctctccctct                                                20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cctccggtag ggccaaggct                                                20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 70
tgacctgtgg gccgctctcc					20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cctccggtag ggccaaggct					20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cagccctgtg aggcatgggc					20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
agtgagagga gcggctgcca					20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ggggctggtg gagctggtga					20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tggagcccca catcctgcgt					20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 76
tgttccccgt gcctggctct                                                  20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tggggcccat cctggggttc                                                  20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tgatggcacg tgttgccccg                                                  20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
accgtggctg accctcctc                                                   20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cgccgggaca caggaagcac                                                  20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ccctggtgag gagccgggag                                                  20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
```

```
gccagggaag gactgcggtg                                               20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cagccagggc aggactcgga                                               20

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gaggtctggt tcggctttc                                                19

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
cagagctggg agggatgag                                                19

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tgcaacagct tcgttggtag                                               20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
taggtccagc aggaagttgg                                               20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gtcggagaag atccgtgaga                                               20
```

```
<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ccaggcatca atgtcatcag                                                    20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
tgtcaaccag acgttccaaa                                                    20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
taacacagct ggtgcctgag                                                    20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92 attcccccctt aaccacttgc                                                   20

<210> SEQ ID NO 93
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
gagggtgtct cgcttggtc                                                     19

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gctgagtagg aaatgggagg t                                                  21

<210> SEQ ID NO 95
```

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ctgcagtcag ggagcagagt                                               20

<210> SEQ ID NO 96
<211> LENGTH: 212
<212> TYPE: DNA
<213> ORGANISM: Homo sapiens

<400> SEQUENCE: 96
caagacacaa gcaggagagc cacaaagcca gccagcttac tgccatcgta gttcagcgta   60
gcgaagttgg cctgcttctc cgcgcagccc gcactgttgc acaccgcat ctgcagctca   120 taccaggtgg cttcctgcag gtcatacagg atgtaggact ggagagaga ggtcctctga   180 gctgtggtcc aaactgtggt cccaaagggc ct                                 212

<210> SEQ ID NO 97
<211> LENGTH: 36
<212> TYPE: DNA
<213> ORGANISM: Homo sapiens

<400> SEQUENCE: 97
tgccatcgta gttcagcgta gcgaagttgg cctgct                             36

<210> SEQ ID NO 98
<211> LENGTH: 36
<212> TYPE: DNA
<213> ORGANISM: Homo sapiens

<400> SEQUENCE: 98
ttggaccaca gctcagagga cctctctctc caagtc                             36

<210> SEQ ID NO 99
<211> LENGTH: 28
<212> TYPE: DNA
<213> ORGANISM: Homo sapiens

<400> SEQUENCE: 99
gtagtcagtg cttcagagtc agagtgga                                      28

<210> SEQ ID NO 100
<211> LENGTH: 28
<212> TYPE: DNA
<213> ORGANISM: Homo sapiens

<400> SEQUENCE: 100
cccccaagag gtgcttgtag tcagtgct                                      28

<210> SEQ ID NO 101
<211> LENGTH: 28
<212> TYPE: DNA
<213> ORGANISM: Homo sapiens

<400> SEQUENCE: 101
cgtgaccccc aagaggtgct tgtagtca                                      28

<210> SEQ ID NO 102
<211> LENGTH: 28
```

<212> TYPE: DNA
<213> ORGANISM: Homo sapiens

<400> SEQUENCE: 102
aacagccgtg accccccaara ggtgcttg        28

<210> SEQ ID NO 103
<211> LENGTH: 28
<212> TYPE: DNA
<213> ORGANISM: Homo sapiens

<400> SEQUENCE: 103
ccatggccac gccaggagcc tggtctca        28

<210> SEQ ID NO 104
<211> LENGTH: 28
<212> TYPE: DNA
<213> ORGANISM: Homo sapiens

<400> SEQUENCE: 104
ccatggccac gccaggagcc tggtctca        28

<210> SEQ ID NO 105
<211> LENGTH: 28
<212> TYPE: DNA
<213> ORGANISM: Homo sapiens

<400> SEQUENCE: 105
caccggggca gctgctgatg cccatggc        28

<210> SEQ ID NO 106
<211> LENGTH: 28
<212> TYPE: DNA
<213> ORGANISM: Homo sapiens

<400> SEQUENCE: 106
aggaagagga ctgtgtcacc ggggcagt        28

<210> SEQ ID NO 107
<211> LENGTH: 28
<212> TYPE: DNA
<213> ORGANISM: Homo sapiens

<400> SEQUENCE: 107
gaggaagagg actgtgttac cggggcag        28

<210> SEQ ID NO 108
<211> LENGTH: 28
<212> TYPE: DNA
<213> ORGANISM: Homo sapiens

<400> SEQUENCE: 108
gagctgagga agaggactgt gtcaccgg        28

<210> SEQ ID NO 109
<211> LENGTH: 28
<212> TYPE: DNA
<213> ORGANISM: Homo sapiens

<400> SEQUENCE: 109
gagtcagagt ggagctgagg aagaggac        28

<210> SEQ ID NO 110
<211> LENGTH: 28

```
<212> TYPE: DNA
<213> ORGANISM: Homo sapiens

<400> SEQUENCE: 110
gatgcccatg gccacgccag gagcctgg                                    28

<210> SEQ ID NO 111
<211> LENGTH: 28
<212> TYPE: DNA
<213> ORGANISM: Homo sapiens

<400> SEQUENCE: 111
gatgcccatg gccacgccag gagcctgg                                    28

<210> SEQ ID NO 112
<211> LENGTH: 28
<212> TYPE: DNA
<213> ORGANISM: Homo sapiens

<400> SEQUENCE: 112
ctgatgccca tggccacgcc aggagcct                                    28

<210> SEQ ID NO 113
<211> LENGTH: 28
<212> TYPE: DNA
<213> ORGANISM: Homo sapiens

<400> SEQUENCE: 113
gtcaccgggg cagttgctga tgcccatg                                    28

<210> SEQ ID NO 114
<211> LENGTH: 28
<212> TYPE: DNA
<213> ORGANISM: Homo sapiens

<400> SEQUENCE: 114
gccaggagcc tggtctcatg agtctcct                                    28

<210> SEQ ID NO 115
<211> LENGTH: 28
<212> TYPE: DNA
<213> ORGANISM: Homo sapiens

<400> SEQUENCE: 115
caccatggca tcaagctcta cccctgcc                                    28

<210> SEQ ID NO 116
<211> LENGTH: 28
<212> TYPE: DNA
<213> ORGANISM: Homo sapiens

<400> SEQUENCE: 116
caccatggca tcaagctcta cccctgcc                                    28

<210> SEQ ID NO 117
<211> LENGTH: 28
<212> TYPE: DNA
<213> ORGANISM: Homo sapiens

<400> SEQUENCE: 117
ccaccatggc atcaagctct acccctgc                                    28

<210> SEQ ID NO 118
<211> LENGTH: 28
```

```
<212> TYPE: DNA
<213> ORGANISM: Homo sapiens

<400> SEQUENCE: 118
cactccacca tggcatcaag ctctaccc                                       28

<210> SEQ ID NO 119
<211> LENGTH: 28
<212> TYPE: DNA
<213> ORGANISM: Homo sapiens

<400> SEQUENCE: 119
cctacactcc accatggcat caagctct                                       28

<210> SEQ ID NO 120
<211> LENGTH: 28
<212> TYPE: DNA
<213> ORGANISM: Homo sapiens

<400> SEQUENCE: 120
cctacactcc accatggcat caagctct                                       28

<210> SEQ ID NO 121
<211> LENGTH: 28
<212> TYPE: DNA
<213> ORGANISM: Homo sapiens

<400> SEQUENCE: 121
agtctccttg tctctgagcc tctcctac                                       28

<210> SEQ ID NO 122
<211> LENGTH: 28
<212> TYPE: DNA
<213> ORGANISM: Homo sapiens

<400> SEQUENCE: 122
tccaccatgg catcaagctc tacccctg                                       28

<210> SEQ ID NO 123
<211> LENGTH: 28
<212> TYPE: DNA
<213> ORGANISM: Homo sapiens

<400> SEQUENCE: 123
tctcctacac tccaccatgg catcaagc                                       28

<210> SEQ ID NO 124
<211> LENGTH: 22
<212> TYPE: DNA
<213> ORGANISM: Homo sapiens

<400> SEQUENCE: 124
ccactaggac ctcctcctgt ct                                             22

<210> SEQ ID NO 125
<211> LENGTH: 26
<212> TYPE: DNA
<213> ORGANISM: Homo sapiens

<400> SEQUENCE: 125
ctcaccacta ggacctcctc ctgtct                                         26

<210> SEQ ID NO 126
<211> LENGTH: 28
```

```
<212> TYPE: DNA
<213> ORGANISM: Homo sapiens

<400> SEQUENCE: 126
cctgcccctg ctcaccacta ggacctcc                                              28

<210> SEQ ID NO 127
<211> LENGTH: 28
<212> TYPE: DNA
<213> ORGANISM: Homo sapiens

<400> SEQUENCE: 127
tctgcccctg ctcaccacta ggacctcc                                              28

<210> SEQ ID NO 128
<211> LENGTH: 28
<212> TYPE: DNA
<213> ORGANISM: Homo sapiens

<400> SEQUENCE: 128
atgcatgtcc tgcccctgct caccacta                                              28

<210> SEQ ID NO 129
<211> LENGTH: 10
<212> TYPE: DNA
<213> ORGANISM: Homo sapiens

<400> SEQUENCE: 129
cctcctgtct                                                                  10

<210> SEQ ID NO 130
<211> LENGTH: 28
<212> TYPE: DNA
<213> ORGANISM: Homo sapiens

<400> SEQUENCE: 130
cagcccccag aagatgcatg tcctgccc                                              28

<210> SEQ ID NO 131
<211> LENGTH: 26
<212> TYPE: DNA
<213> ORGANISM: Homo sapiens

<400> SEQUENCE: 131
ctcaccacta ggacctcctc ctgtct                                                26

<210> SEQ ID NO 132
<211> LENGTH: 28
<212> TYPE: DNA
<213> ORGANISM: Homo sapiens

<400> SEQUENCE: 132
aacagccgtg accccaaga ggtgcttg                                               28

<210> SEQ ID NO 133
<211> LENGTH: 251
<212> TYPE: DNA
<213> ORGANISM: Homo sapiens

<400> SEQUENCE: 133
aacagccgtg accccaaga ggtgcttgta gtcagtgctt cagagtcaga gtggagctga           60
ggaagaggac tgtgtcaccg ggcagttgc tgatgcccat ggccacgcca ggagcctggt          120
ctcatgagtc tccttgtctc tgagcctctc ctacactcca ccatggcatc aagctctacc         180
```

```
cctgcctccc tgcagccccc agaagatgca tgtcctgccc ctgctcacca ctaggacctc    240
ctcctgtctg g                                                         251
```